US006762038B1

(12) United States Patent
Silverman et al.

(10) Patent No.: US 6,762,038 B1
(45) Date of Patent: Jul. 13, 2004

(54) MUTANT CELL LINES AND METHODS FOR PRODUCING ENHANCED LEVELS OF RECOMBINANT PROTEINS

(75) Inventors: Robert H. Silverman, Beachwood, OH (US); Bryan R. G. Williams, Cleveland, OH (US); Fulvia Terenzi, Cleveland, OH (US); Aimin Zhou, Solon, OH (US); Sandy Der, Toronto, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/393,028

(22) Filed: Sep. 9, 1999

Related U.S. Application Data
(60) Provisional application No. 60/099,603, filed on Sep. 9, 1998.

(51) Int. Cl.$^7$ .......................... C12P 21/06; C12N 7/00; C12N 5/00; C12N 15/63; C12N 15/00
(52) U.S. Cl. ................... 435/69.1; 435/235.1; 435/325; 435/455; 435/463; 800/22
(58) Field of Search ................................ 435/325, 463, 435/455, 440, 735.1, 69.1; 800/13, 22

(56) References Cited

U.S. PATENT DOCUMENTS

| | | | | |
|---|---|---|---|---|
| 5,002,874 A | 3/1991 | Kaufman | .................... | 435/69.1 |
| 5,840,565 A | 11/1998 | Lau | .......................... | 435/235.1 |
| 5,990,091 A | 11/1999 | Tartaglia et al. | ............... | 514/44 |
| 6,004,777 A | 12/1999 | Tartaglia et al. | ............ | 435/69.1 |

OTHER PUBLICATIONS

Rudinger, Characteristics of the amino acids as components of a peptide hormone sequence, 1976, edited by Parson's, University Park Press, Baltimore, pp. 1–7.*
Kaye et al., A single amino acid sustitution results in a retinoblastoma protein defective in phosphorylation and oncoprotein binding, 1990, Proc. Natl. Acad. Sci. USA, vol. 87, pp. 6922–6926.*
Eloit et al., Journal of Virology, vol. 71, No. 7, p. 5375–5381, Jul. 1997.*
Yang et al., EMBO Journal, vol. 14, p. 6095–6106, 1995.*
Barber et al., Molecular and Cellular Biology, vol. 15, No. 6, p. 3138–3146, Jun. 1995.*
Zhou et al., EMBO Journal, vol. 16, p. 6355–6363, 1997.*
Eck et al., Goodman & Gilman's The Pharmacological Basis of Therapeutics, Ninth edition, McGraw–Hill, New York, Chap. 5 Gene–Based Therapy, p. 77–101, 1996.*
Palmiter et al., Science, vol. 222, p. 809–814, Nov. 1983.*
Pursel et al., J. Reprod. Fert., Suppl. 40, p. 235–245, 1990.*
Louis–Marie Houdebine, Journal of Biotechnology, 34, p. 269–287, 1994.*
R. F. Seamark, Reprod. Fertil. Dev., 6, 653–657, 1994.*

"Translational Control Mediated by Eucaryotic Initiation Factor–2 Is Restricted to Specific mRNA's in Transfected Cells" by Kaufman, et al., *Molecular and Cellular Biology*, vol. 7, No. 4, Apr. 1987.
"Enhancement of Expression of Exogenous Genes by 2–Aminopurine: Regulation at the Post–Transcriptional Level" by Kalvakolanu, et al., *The Journal of Biological Chemistry*, vol. 266, No. 2, Jan. 15, 1991, pp. 873–879.
"DNA Transfection to Study Translational Control in Mammalian Cells" by Kaufman, *Methods: A Companion to Methods in Enzymology*, 11, 1997, pp. 361–370.
"Induction of Interferon Synthesis and Activation of Interferon–Stimulated Genes by Liposomal Transfection Reagents", by Li, et al., *Journal of Interferon and Cytokine Research*, 18:947–952 (1998).
"A Novel Effect of Adenovirus VA $RNA_1$ on Cytoplasmic mRNA Abundance" by Svensson et al., *Virology*, 174, 613–617 (1990).
"Adenovirus VAI–RNA regulates gene expression by controlling stability of ribosome–bound RNAs" by Strijker, et al., pp. 2669–2675.
"Mechanism for discrimination between viral and host mRNA in inteferon–treated cells" by Nilsen, et al., *Proc. Natl. Acad. Sci. USA*, vol. 76, No. 6, Jun. 1979, pp. 2600–2604.
"Activation of Interferon–inducible 2'–5' Oligoadenylate Synthetase by Adenoviral VAI RNA" by Desai, et al., *The Journal of Biological Chemistry*, vol. 270, No. 7, Feb. 17, 1995, pp. 2454–3461.
"Adenovirus Virus–Associated RNA and Translational Control" by Mathews, et al., *Journal of Virology*, vol. 65, No. 11, Nov. 1991, pp. 5657–5662.
"The Phosphorylation State of Eucaryotic Initiation Factor 2 Alters Translational Efficiency of Specific mRNAs" by Kaufman, et al., *Molecular and Cellular Biology*, vol. 9, No. 3, Mar. 1989, pp. 946–958.

(List continued on next page.)

*Primary Examiner*—Scott D. Priebe
*Assistant Examiner*—Shin-Lin Chen
(74) *Attorney, Agent, or Firm*—Calfee, Halter & Griswold LLP

(57) ABSTRACT

Mammalian somatic cells having a homozygous disruption in the gene which encodes the endonbonuclease RNase L and a homyzgous disruption in the gene which encodes the double-stranded RNA dependent kinase PKR are provided. Methods for producing enhanced levels of recombinant proteins in mammalian cell systems are also provided. In one aspect the method employs cells having a homozygous disruption in the RNase L gene and a homozygous disruption in the PKR gene and comprises transfecting the cells with a nucleic acid, or polynucleotide, encoding a desired, exogenous protein; expressing the exogenous protein in the cell; and isolating the exogenous protein from the transfected cells. In another aspect the method employs RNase L null cells transfected with a nucleic acid encoding a desired, exogenous protein. In another aspect the methods employ mutant cells hating a homozygous disruption in the PKR gene, i.e. PKR null cells.

12 Claims, 17 Drawing Sheets

OTHER PUBLICATIONS

"Interferon action and aptosis are defective in mice devoid of 2', 5'–oligoadenylate–dependent RNase L" by Zhou, et al., *The EMBO Journal,* vol. 16, No. 21, pp. 6355–6363.

Product Literature for pAdVAntage™ Vector, p. 266.

"Inhibition of mRNA binding to ribosomes by localized activation of dsRNA–dependent protein kinase" by Benedetti, et al., *Letters to Nature,* vol. 311, Sep. 1984, pp. 79–81.

"Overview of Vestor Design for Mammalian Gene Expression" by Kaufman, *Methods in Molecular Biology,* vol. 62: Recombinant Gene Expression Protocols, pp. 287–300.

"The antiviral enzymes PKR and RNase L suppress gene expression from viral and non–viral based vectors" by Terenzi, et al., *Nucleic Acids Research,* vol. 27, No. 22, 1999, pp. 4369–4375.

Abstract #P201, "Genomic Organization and Promoter Structure of the Human RNase L gene" by Zhou, et al., 1999 Annual Meeting of the International Society for Interferon & Cytokine Research, Paris, France, Sep. 5–9, 1999.

Abstract #P203, "Boosting Expression of Exogenous Genes by Suppressing the Cellular Enzymes PKR and RNase L" by Terenzi, et al., 1999 Annual Meeting of the International Society for Interferon & Cytokine Research, Paris, France, Sep. 5–9, 1999.

* cited by examiner

Fig. 13A

-163
attcggcacgaggaaggtgccaattactagctcccttctttattcgtgta ctgatgagatgtcagaagacagaacataatcagcccaatccctactccaa gactctcattgtgtcccaaagaaacacacgtgtgcatttcccaaggaaaa

| ggcattgaggacc | ATG GAG ACC CCG GAT TAT | 18 |
|---|---|---|
| | Met Glu Thr Pro Asp Tyr | 6 |

| AAC ACA CCT CAG GGT GGA ACC CCA TCA GCG | 48 |
|---|---|
| Asn Thr Pro Gln Gly Gly Thr Pro Ser Ala | 16 |

| GGA AGT CAG AGG ACC GTT CTC GAA GAT GAT | 78 |
|---|---|
| Gly Ser Gln Arg Thr Val Val Glu Asp Asp | 26 |

| TCT TCG TTG ATC AAA GCT GTT CAG AAG GGA | 108 |
|---|---|
| Ser Ser Leu Ile Lys Ala Val Gln Lys Gly | 36 |

| GAT GTT GTC AGG GTC CAG CAA TTG TTA GAA | 138 |
|---|---|
| Asp Val Val Arg Val Gln Gln Leu Leu Glu | 46 |

| AAA GGG GCT GAT GCC AAT GCC TGT GAA GAC | 128 |
|---|---|
| Lys Gly Ala Asp Ala Asn Ala Cys Glu Asp | 56 |

| ACC TGG GGC TGG ACA CCT TTG CAC AAC GCA | 198 |
|---|---|
| Thr Trp Gly Trp Thr Pro Leu His Asn Ala | 66 |

| GTG CAA GCT GGC AGG GTA GAC ATT GTG AAC | 228 |
|---|---|
| Val Gln Ala Gly Arg Val Asp Ile Val Asn | 76 |

| CTC CTG CTT AGT CAT GGT GCT GAC CCT CAT | 258 |
|---|---|
| Leu Leu Leu Ser His Gly Ala Asp Pro His | 86 |

| CGG AGG AAG AAG AAT GGG GCC ACC CCC TTC | 288 |
|---|---|
| Arg Arg Lys Lys Asn Gly Ala Thr Pro Phe | 96 |

| ATC ATT GCT GGG ATC CAG GGA GAT GTG AAA | 318 |
|---|---|
| Ile Ile Ala Gly Ile Gln Gly Asp Val Lys | 106 |

| CTG CTC GAG ATT CTC CTC TCT TGT GGT GCA | 348 |
|---|---|
| Leu Leu Glu Ile Leu Leu Ser Cys Gly Ala | 116 |

Fig. 13B

```
GAC GTC AAT GAG TGT GAC GAG AAC GGA TTC           378
Asp Val Asn Glu Cys Asp Glu Asn Gly Phe           126

ACG GCT TTC ATG GAA GCT GCT GAG CGT GGT           408
Thr Ala Phe Met Glu Ala Ala Glu Arg Gly           136

AAC GCT GAA GCC TTA AGA TTC CTT TTT GCT           438
Asn Ala Glu Ala Leu Arg Phe Leu Phe Ala           146

AAG GGA GCC AAT GTG AAT TTG CGA CGA CAG           468
Lys Gly Ala Asn Val Asn Leu Arg Arg Gln           156

ACA ACG AAG GAC AAA AGG CGA TTG AAG CAA           498
Thr Thr Lys Asp Lys Arg Arg Leu Lys Gln           166

GGA GGC GCC ACA GCT CTC ATG AGC GCT GCT           528
Gly Gly Ala Thr Ala Leu Met Ser Ala Ala           176

GAG AAG GGC CAC CTG GAA GTC CTG AGA ATT           558
Leu Leu Asn Asp Met Lys Ala Glu Val Asp           196

GCT CGG GAC AAC ATG GGC AGA AAT GCC CTG           618
Ala Arg Asp Asn Met Gly Arg Asn Ala Leu           206

ATC CGT ACT CTG CTG AAC TGG GAT TGT GAA           648
Ile Arg Thr Leu Leu Asn Trp Asp Cys Glu           216

AAT GTG GAG GAG ATT ACT TCA ATC CTG ATT           678
Asn Val Glu Glu Ile Thr Ser Ile Leu Ile           226

CAG CAC GGG GCT GAT GTT AAC GTG AGA GAA           708
Gln His Gly Ala Asp Val Asn Val Arg Gly           236

GAA AGA GGG AAA ACA CCC CTC ATC GCA GCA           738
Glu Arg Gly Lys Thr Pro Leu Ila Ala Ala           246

GTG GAG AGG AAG CAC ACA GGC TTG GTG CAG           768
Val Glu Arg Lys His Thr Gly Leu Val Gln           256

ATG CTC CTG AGT CGG GAA GGC ATA AAC ATA           798
Met Leu Leu Ser Arg Glu Gly Ile Asn Ile           266
```

Fig. 13C

```
GAT GCC AGG GAT AAC GAG GGC AAG ACA GCT           828
Asp Ala Arg Asp Asn Glu Gly Lys Thr Ala           276

CTG CTA ATT GCT GTT GAT AAA CAA CTG AAG           858
Leu Leu Ile Ala Val Asp Lys Gln Leu Lys           286

GAA ATT GTC CAG TTG CTT CTT GAA AAG GGA           888
Glu Ile Val Gln Leu Leu Leu Glu Lys Gly           296

GCT GAT AAG TGT GAC GAT CTT GTT TGG ATA           918
Ala Asp Lys Cys Asp Asp Leu Val Trp Ile           306

GCC AGG AGG AAT CAT GAC TAT CAC CTT GTA           948
Ala Arg Arg Asn His Asp Tyr His Leu Val           316

AAG CTT CTC CTC CTT TAT GTA GCT AAT CCT           978
Lys Leu Leu LEu Pro Tyr Val Ala Asn Pro           326

GAC ACC GAC CCT CCT GCT GGA GAC TGG TCG          1008
Asp Thr Asp Pro Pro Ala Gly Asp Trp Ser           336

CCT CAC AGT TCA CGT TGG GGG ACA GCC TTG          1038
Pro His Ser Ser Arg Trp Gly Thr Ala Leu           346

AAA AGC CTC CAC AGT ATG ACT CGA CCC ATG          1068
Lys Ser Leu His Ser Met Thr Arg Pro Met           356

ATT GGC AAA CTC AAG ATC TTC ATT CAT GAT          1098
Ile Gly Lys Leu Lys Ile Phe Ile His Asp           366

GAC TAT AAA ATT GCT GGC ACT TCC GAA GGG          1128
Asp Tyr Lys Ile Ala Gly Thr Ser Glu Gly           376

GCT GTC TAC CTA GGG ATC TAT GAC AAT GGA          1158
Ala Val Tyr Leu Gly Ile Tyr Asp Asn Arg           386

GAA GTG GCT GTG AAG GTC TTC CGT GAG AAT          1188
Glu Val Ala Val Lys Val Phe Arg Glu Asn           396

AGC CCA CGT GGA TGT AAG GAA TGTC TCT TGT         1218
Ser Pro Arg Gly Cys Lys Glu Val Ser Cys          406
```

Fig. 13D

```
CTG CGG GAC TGC GGT GAC CAC AGT AAC TTA           1248
Leu Arg Asp Cys Gly Asp His Ser Asn Leu            416

GTG GCT TTC TAT GGA AGA GAG GAC GAT AAG           1278
Val Ala Phe Tyr Gly Arg Glu Asp Asp Lys            426

GGC TGT TTA TAT GTG TGT GTG TCC CTG TGT           1308
Gly Cys Leu Tyr Val Cys Val Ser Leu Cys            436

GAG TGG ACA CTG GAA GAG TTC CTG AGG TTG           1338
Glu Trp Thr Leu Glu Glu Phe Leu Arg Leu            446

CCC AGA GAG GAA CCT GTG GAG AAC GGG GAA           1368
Pro Arg Glu Glu Pro Val Glu Asn Gly Glu            456

GAT AAG TTT GCC CAC AGC ATC CTA TTA TCT           1398
Asp Lys Phe Ala His Ser Ile Leu Leu Ser            466

ATA TTT GAG GGT GTT CAA AAA CTA CAC TTG           1428
Ile Phe Glu Gly Val Gln Lys Leu His Leu            476

CAT GGA TAT TCC CAT CAG GAC CTG CAA CCA           1458
His Gly Tyr Ser His Gln Asp Leu Gln Pro            486

CAA AAC ATC TTA ATA GAT TCC AAG AAA GCT           1488
Gln Asn Ile Leu Ile Asp Ser Lys Lys Ala            496

GTC CGG CTG GCA GAT TTT GAT CAG AGC ATC           1518
Val Arg Leu Ala Asp Phe Asp Gln Ser Ile            506

CGA TGG ATG GGA GAG TCA CAG ATG GTC AGG           1548
Arg Trp Met Gly Glu Ser Gln Met Val Arg            516

AGA GAC TTG GAG GAT CTT GGA CGG CTG GTT           1578
Arg Asp Leu Glu Asp Leu Gly ARg Leu Val            526

CTC TAC GTG GTA ATG AAA GGT GAG ATC CCC           1608
Leu Tyr Val Val Met Lys Gly Glu Ile Pro            536

TTT GAG ACA CTA AAG ACT CAG AAT GAT GAA           1638
Phe Glu Ghr Leu Lys Thr Gln Asn Asp Glu            546
```

Fig. 13E

| | |
|---|---|
| GTG CTG CTT ACA ATG TCT CCA GAT GAG GAG | 1668 |
| Val Leu Leu Thr Met Ser Pro Asp Glu Glu | 556 |
| | |
| ACT AAG GAC CTC ATT CAT TGC CTG TTT TCT | 1698 |
| Thr Lys Asp Leu Ile His Cys Leu Phe Ser | 566 |
| | |
| CCT GGA GAA AAT GTC AAG AAC TGC CTG GTA | 1728 |
| Pro Gly Glu Asn Val Lys Asn Cys Leu Val | 576 |
| | |
| GAC CTG CTT GGC CAT CCT TTC TTT TGG ACT | 1758 |
| Asp Leu Leu Gly His Pro Phe Phe Trp Thr | 586 |
| | |
| TGG GAG AAC CGC TAT AGA ACA CTC CGG AAT | 1788 |
| Trp Glu Asn Arg Tyr Arg Thr Leu Arg Asn | 596 |
| | |
| GTG GGA AAT GAA TCT GAC ATC AAA GTA CGG | 1818 |
| Val Gly Asn Glu Ser Asp Ile Lys Val Arg | 606 |
| | |
| AAA TGT AAA AGT GAT CTT CTC AGA CTA CTG | 1848 |
| Lys Cys Lys Ser Asp Leu LEu Arg Leu Leu | 616 |
| | |
| CAG CAT CAG ACA CTT GAG CCT CCC AGA AGC | 1878 |
| Gln His Gln Thr Leu Glu Pro Pro Arg Ser | 626 |
| | |
| TTT GAC CAG TGG ACA TGT AAG ATC GAC AAA | 1908 |
| Phe Asp Gln Trp Thr Ser Lys Ile Asp Lys | 636 |
| | |
| AAT GTT ATG GAT GAA ATG AAT CAT TTC TAC | 1938 |
| Asn Val Met Asp Glu Met Asn His Phe Tyr | 646 |
| | |
| GAA AAG AGA AAA AAA AAC CCT TAT CAG GAT | 1968 |
| Glu Lys Arg Lys Lys Asn Pro Tyr Gln Asp | 656 |
| | |
| ACT GTA GGT GAT CTG CTG AAG TTT ATT CGG | 1998 |
| Thr Val Gly Asp Leu Leu Lys Phe Ile Arg | 666 |
| | |
| AAT ATA GGC GAA CAC ATC AAT GAG GAA AAA | 2028 |
| Asn Ile Gly Glu His Ile Asn GLu Glu Lys | 676 |
| | |
| AAG CGG GGG | 2037 |
| Lys Arg Gly | 679 |

SEQUENCE LISTING

```
<160> NUMBER OF SEQ ID NOS: 5

<210> SEQ ID NO 1
<211> LENGTH: 2200
<212> TYPE: DNA
<213> ORGANISM: RNase L
<220> FEATURE:
<221> NAME/KEY: CDS
<222> LOCATION: (164)..(2200)

<400> SEQUENCE: 1
attcggcacg aggaaggtgc caattactag ctcccttctt tattcgtgta ctgatgagat        60
gtcagaagac agaacataat cagcccaatc cctactccaa gactctcatt gtgtcccaaa       120
gaaacacacg tgtgcatttc ccaaggaaaa ggcattgagg acc atg gag acc ccg        175
                                              Met Glu Thr Pro
                                                1 gat tat aac aca cct cag ggt gga acc cca tca gcg gga agt cag agg        223
Asp Tyr Asn Thr Pro Gln Gly Gly Thr Pro Ser Ala Gly Ser Gln Arg
 5                  10                  15                  20 acc gtt gtc gaa gat gat tct tcg ttg atc aaa gct gtt cag aag gga        271
Thr Val Val Glu Asp Asp Ser Ser Leu Ile Lys Ala Val Gln Lys Gly
                25                  30                  35 gat gtt gtc agg gtc cag caa ttg tta gaa aaa ggg gct gat gcc aat        319
Asp Val Val Arg Val Gln Gln Leu Leu Glu Lys Gly Ala Asp Ala Asn
            40                  45                  50 gcc tgt gaa gac acc tgg ggc tgg aca cct ttg cac aac gca gtg caa        367
Ala Cys Glu Asp Thr Trp Gly Trp Thr Pro Leu His Asn Ala Val Gln
        55                  60                  65
```

-continued

```
gct ggc agg gta gac att gtg aac ctc ctg ctt agt cat ggt gct gac      415
Ala Gly Arg Val Asp Ile Val Asn Leu Leu Leu Ser His Gly Ala Asp
 70              75                  80 cct cat cgg agg aag aag aat ggg gcc acc ccc ttc atc att gct ggg      463
Pro His Arg Arg Lys Lys Asn Gly Ala Thr Pro Phe Ile Ile Ala Gly
 85              90                  95                 100 atc cag gga gat gtg aaa ctg ctc gag att ctc ctc tct tgt ggt gca      511
Ile Gln Gly Asp Val Lys Leu Leu Glu Ile Leu Leu Ser Cys Gly Ala
                105                 110                 115 gac gtc aat gag tgt gac gag aac gga ttc acg gct ttc atg gaa gct      559
Asp Val Asn Glu Cys Asp Glu Asn Gly Phe Thr Ala Phe Met Glu Ala
120                 125                 130 gct gag cgt ggt aac gct gaa gcc tta aga ttc ctt ttt gct aag gga      607
Ala Glu Arg Gly Asn Ala Glu Ala Leu Arg Phe Leu Phe Ala Lys Gly
        135                 140                 145 gcc aat gtg aat ttg cga cga cag aca acg aag gac aaa agg cga ttg      655
Ala Asn Val Asn Leu Arg Arg Gln Thr Thr Lys Asp Lys Arg Arg Leu
    150                 155                 160 aag caa gga ggc gcc aca gct ctc atg agc gct gct gag aag ggc cac      703
Lys Gln Gly Gly Ala Thr Ala Leu Met Ser Ala Ala Glu Lys Gly His
165                 170                 175                 180 ctg gaa gtc ctg aga att ctc ctc aat gac atg aag gca gaa gtc gat      751
Leu Glu Val Leu Arg Ile Leu Leu Asn Asp Met Lys Ala Glu Val Asp
                185                 190                 195 gct cgg gac aac atg ggc aga aat gcc ctg atc cgt act ctg ctg aac      799
Ala Arg Asp Asn Met Gly Arg Asn Ala Leu Ile Arg Thr Leu Leu Asn
                200                 205                 210 tgg gat tgt gaa aat gtg gag gag att act tca atc ctg att cag cac      847
Trp Asp Cys Glu Asn Val Glu Glu Ile Thr Ser Ile Leu Ile Gln His
        215                 220                 225 ggg gct gat gtt aac gtg aga gaa gaa aga ggg aaa aca ccc ctc atc      895
Gly Ala Asp Val Asn Val Arg Glu Glu Arg Gly Lys Thr Pro Leu Ile
230                 235                 240 gca gca gtg gag agg aag cac aca ggc ttg gtg cag atg ctc ctg agt      943
Ala Ala Val Glu Arg Lys His Thr Gly Leu Val Gln Met Leu Leu Ser
245                 250                 255                 260 cgg gaa ggc ata aac ata gat gcc agg gat aac gag ggc aag aca gct      991
Arg Glu Gly Ile Asn Ile Asp Ala Arg Asp Asn Glu Gly Lys Thr Ala
                265                 270                 275 ctg cta att gct gtt gat aaa caa ctg aag gaa att gtc cag ttg ctt     1039
Leu Leu Ile Ala Val Asp Lys Gln Leu Lys Glu Ile Val Gln Leu Leu
                280                 285                 290 ctt gaa aag gga gct gat aag tgt gac gat ctt gtt tgg ata gcc agg     1087
Leu Glu Lys Gly Ala Asp Lys Cys Asp Asp Leu Val Trp Ile Ala Arg
            295                 300                 305 agg aat cat gac tat cac ctt gta aag ctt ctc ctc ctt tat gta gct     1135
Arg Asn His Asp Tyr His Leu Val Lys Leu Leu Leu Leu Tyr Val Ala
310                 315                 320 aat cct gac acc gac cct cct gct gga gac tgg tcg cct cac agt tca     1183
Asn Pro Asp Thr Asp Pro Pro Ala Gly Asp Trp Ser Pro His Ser Ser
325                 330                 335                 340 cgt tgg ggg aca gcc ttg aaa agc ctc cac agt atg act cga ccc atg     1231
Arg Trp Gly Thr Ala Leu Lys Ser Leu His Ser Met Thr Arg Pro Met
                345                 350                 355 att ggc aaa ctc aag atc ttc att cat gat gac tat aaa att gct ggc     1279
Ile Gly Lys Leu Lys Ile Phe Ile His Asp Asp Tyr Lys Ile Ala Gly
                360                 365                 370 act tcc gaa ggg gct gtc tac cta ggg atc tat gac aat cga gaa gtg     1327
Thr Ser Glu Gly Ala Val Tyr Leu Gly Ile Tyr Asp Asn Arg Glu Val
```

|  |  |  |  |  |  |  |  |  |  |  |  |  |
|---|---|---|---|---|---|---|---|---|---|---|---|---|
|  |  | 375 |  |  |  | 380 |  |  |  | 385 |  |  |
| gct | gtg | aag | gtc | ttc | cgt | gag | aat | agc | cca | cgt | gga | tgt | aag | gaa | gtc | 1375 |
| Ala | Val | Lys | Val | Phe | Arg | Glu | Asn | Ser | Pro | Arg | Gly | Cys | Lys | Glu | Val |  |
|  | 390 |  |  |  |  | 395 |  |  |  | 400 |  |  |  |  |  |
| tct | tgt | ctg | cgg | gac | tgc | ggt | gac | cac | agt | aac | tta | gtg | gct | ttc | tat | 1423 |
| Ser | Cys | Leu | Arg | Asp | Cys | Gly | Asp | His | Ser | Asn | Leu | Val | Ala | Phe | Tyr |  |
| 405 |  |  |  |  | 410 |  |  |  |  | 415 |  |  |  |  | 420 |  |
| gga | aga | gag | gac | gat | aag | ggc | tgt | tta | tat | gtg | tgt | gtg | tcc | ctg | tgt | 1471 |
| Gly | Arg | Glu | Asp | Asp | Lys | Gly | Cys | Leu | Tyr | Val | Cys | Val | Ser | Leu | Cys |  |
|  |  |  |  | 425 |  |  |  |  | 430 |  |  |  |  | 435 |  |  |
| gag | tgg | aca | ctg | gaa | gag | ttc | ctg | agg | ttg | ccc | aga | gag | gaa | cct | gtg | 1519 |
| Glu | Trp | Thr | Leu | Glu | Glu | Phe | Leu | Arg | Leu | Pro | Arg | Glu | Glu | Pro | Val |  |
|  |  |  | 440 |  |  |  |  | 445 |  |  |  |  | 450 |  |  |  |
| gag | aac | ggg | gaa | gat | aag | ttt | gcc | cac | agc | atc | cta | tta | tct | ata | ttt | 1567 |
| Glu | Asn | Gly | Glu | Asp | Lys | Phe | Ala | His | Ser | Ile | Leu | Leu | Ser | Ile | Phe |  |
|  |  |  | 455 |  |  |  |  | 460 |  |  |  |  | 465 |  |  |  |
| gag | ggt | gtt | caa | aaa | cta | cac | ttg | cat | gga | tat | tcc | cat | cag | gac | ctg | 1615 |
| Glu | Gly | Val | Gln | Lys | Leu | His | Leu | His | Gly | Tyr | Ser | His | Gln | Asp | Leu |  |
| 470 |  |  |  |  | 475 |  |  |  |  | 480 |  |  |  |  |  |  |
| caa | cca | caa | aac | atc | tta | ata | gat | tcc | aag | aaa | gct | gtc | cgg | ctg | gca | 1663 |
| Gln | Pro | Gln | Asn | Ile | Leu | Ile | Asp | Ser | Lys | Lys | Ala | Val | Arg | Leu | Ala |  |
| 485 |  |  |  |  | 490 |  |  |  |  | 495 |  |  |  |  | 500 |  |
| gat | ttt | gat | cag | agc | atc | cga | tgg | atg | gga | gag | tca | cag | atg | gtc | agg | 1711 |
| Asp | Phe | Asp | Gln | Ser | Ile | Arg | Trp | Met | Gly | Glu | Ser | Gln | Met | Val | Arg |  |
|  |  |  |  | 505 |  |  |  |  | 510 |  |  |  |  | 515 |  |  |
| aga | gac | ttg | gag | gat | ctt | gga | cgg | ctg | gtt | ctc | tac | gtg | gta | atg | aaa | 1759 |
| Arg | Asp | Leu | Glu | Asp | Leu | Gly | Arg | Leu | Val | Leu | Tyr | Val | Val | Met | Lys |  |
|  |  |  | 520 |  |  |  |  | 525 |  |  |  |  | 530 |  |  |  |
| ggt | gag | atc | ccc | ttt | gag | aca | cta | aag | act | cag | aat | gat | gaa | gtg | ctg | 1807 |
| Gly | Glu | Ile | Pro | Phe | Glu | Thr | Leu | Lys | Thr | Gln | Asn | Asp | Glu | Val | Leu |  |
|  |  | 535 |  |  |  |  | 540 |  |  |  |  | 545 |  |  |  |  |
| ctt | aca | atg | tct | cca | gat | gag | gag | act | aag | gac | ctc | att | cat | tgc | ctg | 1855 |
| Leu | Thr | Met | Ser | Pro | Asp | Glu | Glu | Thr | Lys | Asp | Leu | Ile | His | Cys | Leu |  |
| 550 |  |  |  |  | 555 |  |  |  |  | 560 |  |  |  |  |  |  |
| ttt | tct | cct | gga | gaa | aat | gtc | aag | aac | tgc | ctg | gta | gac | ctg | ctt | ggc | 1903 |
| Phe | Ser | Pro | Gly | Glu | Asn | Val | Lys | Asn | Cys | Leu | Val | Asp | Leu | Leu | Gly |  |
| 565 |  |  |  |  | 570 |  |  |  |  | 575 |  |  |  |  | 580 |  |
| cat | cct | ttc | ttt | tgg | act | tgg | gag | aac | gcg | tat | aga | aca | ctc | cgg | aat | 1951 |
| His | Pro | Phe | Phe | Trp | Thr | Trp | Glu | Asn | Ala | Tyr | Arg | Thr | Leu | Arg | Asn |  |
|  |  |  |  | 585 |  |  |  |  | 590 |  |  |  |  | 595 |  |  |
| gtg | gga | aat | gaa | tct | gac | atc | aaa | gta | cgg | aaa | tgt | aaa | agt | gat | ctt | 1999 |
| Val | Gly | Asn | Glu | Ser | Asp | Ile | Lys | Val | Arg | Lys | Cys | Lys | Ser | Asp | Leu |  |
|  |  |  | 600 |  |  |  |  | 605 |  |  |  |  | 610 |  |  |  |
| ctc | aga | cta | ctg | gac | cat | cag | aca | ctt | gag | cct | ccc | aga | agc | ttt | gac | 2047 |
| Leu | Arg | Leu | Leu | Asp | His | Gln | Thr | Leu | Glu | Pro | Pro | Arg | Ser | Phe | Asp |  |
|  |  | 615 |  |  |  |  | 620 |  |  |  |  | 625 |  |  |  |  |
| cag | tgg | aca | tgt | aag | atc | gac | aaa | aat | gtt | atg | gat | gaa | atg | aat | cat | 2095 |
| Gln | Trp | Thr | Cys | Lys | Ile | Asp | Lys | Asn | Val | Met | Asp | Glu | Met | Asn | His |  |
| 630 |  |  |  |  | 635 |  |  |  |  | 640 |  |  |  |  |  |  |
| ttc | tac | gaa | aag | aga | aaa | aaa | aac | cct | tat | cag | gat | act | gta | ggt | gat | 2143 |
| Phe | Tyr | Glu | Lys | Arg | Lys | Lys | Asn | Pro | Tyr | Gln | Asp | Thr | Val | Gly | Asp |  |
| 645 |  |  |  |  | 650 |  |  |  |  | 655 |  |  |  |  | 660 |  |
| ctg | ctg | aag | ttt | att | cgg | aat | ata | ggc | gaa | cac | atc | aat | gag | gaa | aaa | 2191 |
| Leu | Leu | Lys | Phe | Ile | Arg | Asn | Ile | Gly | Glu | His | Ile | Asn | Glu | Glu | Lys |  |
|  |  |  |  | 665 |  |  |  |  | 670 |  |  |  |  | 675 |  |  |
| aag | cgg | ggg |  |  |  |  |  |  |  |  |  |  |  |  |  | 2200 |
| Lys | Arg | Gly |  |  |  |  |  |  |  |  |  |  |  |  |  |  |

<210> SEQ ID NO 2

```
<211> LENGTH: 679
<212> TYPE: PRT
<213> ORGANISM: RNase L

<400> SEQUENCE: 2
```

| | | | | | | | | | | | | | | |
|---|---|---|---|---|---|---|---|---|---|---|---|---|---|---|
| Met | Glu | Thr | Pro | Asp | Tyr | Asn | Thr | Pro | Gln | Gly | Gly | Thr | Pro | Ser | Ala |
| 1 | | | | 5 | | | | | 10 | | | | | 15 | |
| Gly | Ser | Gln | Arg | Thr | Val | Val | Glu | Asp | Asp | Ser | Ser | Leu | Ile | Lys | Ala |
| | | | 20 | | | | | 25 | | | | | 30 | | |
| Val | Gln | Lys | Gly | Asp | Val | Val | Arg | Val | Gln | Gln | Leu | Leu | Glu | Lys | Gly |
| | | 35 | | | | | 40 | | | | | 45 | | | |
| Ala | Asp | Ala | Asn | Ala | Cys | Glu | Asp | Thr | Trp | Gly | Trp | Thr | Pro | Leu | His |
| | 50 | | | | | 55 | | | | | 60 | | | | |
| Asn | Ala | Val | Gln | Ala | Gly | Arg | Val | Asp | Ile | Val | Asn | Leu | Leu | Leu | Ser |
| 65 | | | | | 70 | | | | | 75 | | | | | 80 |
| His | Gly | Ala | Asp | Pro | His | Arg | Arg | Lys | Lys | Asn | Gly | Ala | Thr | Pro | Phe |
| | | | | 85 | | | | | 90 | | | | | 95 | |
| Ile | Ile | Ala | Gly | Ile | Gln | Gly | Asp | Val | Lys | Leu | Leu | Glu | Ile | Leu | Leu |
| | | | 100 | | | | | 105 | | | | | 110 | | |
| Ser | Cys | Gly | Ala | Asp | Val | Asn | Glu | Cys | Asp | Glu | Asn | Gly | Phe | Thr | Ala |
| | | 115 | | | | | 120 | | | | | 125 | | | |
| Phe | Met | Glu | Ala | Ala | Glu | Arg | Gly | Asn | Ala | Glu | Ala | Leu | Arg | Phe | Leu |
| | 130 | | | | | 135 | | | | | 140 | | | | |
| Phe | Ala | Lys | Gly | Ala | Asn | Val | Asn | Leu | Arg | Arg | Gln | Thr | Thr | Lys | Asp |
| 145 | | | | | 150 | | | | | 155 | | | | | 160 |
| Lys | Arg | Arg | Leu | Lys | Gln | Gly | Gly | Ala | Thr | Ala | Leu | Met | Ser | Ala | Ala |
| | | | | 165 | | | | | 170 | | | | | 175 | |
| Glu | Lys | Gly | His | Leu | Glu | Val | Leu | Arg | Ile | Leu | Leu | Asn | Asp | Met | Lys |
| | | | 180 | | | | | 185 | | | | | 190 | | |
| Ala | Glu | Val | Asp | Ala | Arg | Asp | Asn | Met | Gly | Arg | Asn | Ala | Leu | Ile | Arg |
| | | 195 | | | | | 200 | | | | | 205 | | | |
| Thr | Leu | Leu | Asn | Trp | Asp | Cys | Glu | Asn | Val | Glu | Glu | Ile | Thr | Ser | Ile |
| | 210 | | | | | 215 | | | | | 220 | | | | |
| Leu | Ile | Gln | His | Gly | Ala | Asp | Val | Asn | Val | Arg | Glu | Glu | Arg | Gly | Lys |
| 225 | | | | | 230 | | | | | 235 | | | | | 240 |
| Thr | Pro | Leu | Ile | Ala | Ala | Val | Glu | Arg | Lys | His | Thr | Gly | Leu | Val | Gln |
| | | | | 245 | | | | | 250 | | | | | 255 | |
| Met | Leu | Leu | Ser | Arg | Glu | Gly | Ile | Asn | Ile | Asp | Ala | Arg | Asp | Asn | Glu |
| | | | 260 | | | | | 265 | | | | | 270 | | |
| Gly | Lys | Thr | Ala | Leu | Leu | Ile | Ala | Val | Asp | Lys | Gln | Leu | Lys | Glu | Ile |
| | | 275 | | | | | 280 | | | | | 285 | | | |
| Val | Gln | Leu | Leu | Leu | Glu | Lys | Gly | Ala | Asp | Lys | Cys | Asp | Asp | Leu | Val |
| | 290 | | | | | 295 | | | | | 300 | | | | |
| Trp | Ile | Ala | Arg | Arg | Asn | His | Asp | Tyr | His | Leu | Val | Lys | Leu | Leu | Leu |
| 305 | | | | | 310 | | | | | 315 | | | | | 320 |
| Leu | Tyr | Val | Ala | Asn | Pro | Asp | Thr | Asp | Pro | Pro | Ala | Gly | Asp | Trp | Ser |
| | | | | 325 | | | | | 330 | | | | | 335 | |
| Pro | His | Ser | Ser | Arg | Trp | Gly | Thr | Ala | Leu | Lys | Ser | Leu | His | Ser | Met |
| | | | 340 | | | | | 345 | | | | | 350 | | |
| Thr | Arg | Pro | Met | Ile | Gly | Lys | Leu | Lys | Ile | Phe | Ile | His | Asp | Asp | Tyr |
| | | 355 | | | | | 360 | | | | | 365 | | | |
| Lys | Ile | Ala | Gly | Thr | Ser | Glu | Gly | Ala | Val | Tyr | Leu | Gly | Ile | Tyr | Asp |
| | 370 | | | | | 375 | | | | | 380 | | | | |
| Asn | Arg | Glu | Val | Ala | Val | Lys | Val | Phe | Arg | Glu | Asn | Ser | Pro | Arg | Gly |

-continued

```
                    385                 390                 395                 400
        Cys Lys Glu Val Ser Cys Leu Arg Asp Cys Gly Asp His Ser Asn Leu
                        405                 410                 415
        Val Ala Phe Tyr Gly Arg Glu Asp Lys Gly Cys Leu Tyr Val Cys
                    420                 425                 430
        Val Ser Leu Cys Glu Trp Thr Leu Glu Glu Phe Leu Arg Leu Pro Arg
                        435                 440                 445
        Glu Glu Pro Val Glu Asn Gly Glu Asp Lys Phe Ala His Ser Ile Leu
            450                 455                 460
        Leu Ser Ile Phe Glu Gly Val Gln Lys Leu His Leu His Gly Tyr Ser
        465                 470                 475                 480
        His Gln Asp Leu Gln Pro Gln Asn Ile Leu Ile Asp Ser Lys Lys Ala
                        485                 490                 495
        Val Arg Leu Ala Asp Phe Asp Gln Ser Ile Arg Trp Met Gly Glu Ser
                    500                 505                 510
        Gln Met Val Arg Arg Asp Leu Glu Asp Leu Gly Arg Leu Val Leu Tyr
                    515                 520                 525
        Val Val Met Lys Gly Glu Ile Pro Phe Glu Thr Leu Lys Thr Gln Asn
                    530                 535                 540
        Asp Glu Val Leu Leu Thr Met Ser Pro Asp Glu Glu Thr Lys Asp Leu
        545                 550                 555                 560
        Ile His Cys Leu Phe Ser Pro Gly Glu Asn Val Lys Asn Cys Leu Val
                        565                 570                 575
        Asp Leu Leu Gly His Pro Phe Phe Trp Thr Trp Glu Asn Ala Tyr Arg
                    580                 585                 590
        Thr Leu Arg Asn Val Gly Asn Glu Ser Asp Ile Lys Val Arg Lys Cys
                    595                 600                 605
        Lys Ser Asp Leu Leu Arg Leu Leu Asp His Gln Thr Leu Glu Pro Pro
            610                 615                 620
        Arg Ser Phe Asp Gln Trp Thr Cys Lys Ile Asp Lys Asn Val Met Asp
        625                 630                 635                 640
        Glu Met Asn His Phe Tyr Glu Lys Arg Lys Asn Pro Tyr Gln Asp
                        645                 650                 655
        Thr Val Gly Asp Leu Leu Lys Phe Ile Arg Asn Ile Gly Glu His Ile
                    660                 665                 670
        Asn Glu Glu Lys Lys Arg Gly
                    675

<210> SEQ ID NO 3
<211> LENGTH: 28
<212> TYPE: DNA
<213> ORGANISM: RNase L

<400> SEQUENCE: 3
gtttggctat ttctctgtgt tcattgga                                    28

<210> SEQ ID NO 4
<211> LENGTH: 26
<212> TYPE: DNA
<213> ORGANISM: RNase L

<400> SEQUENCE: 4
gtaatggcta ctccgtgcat ctgggc                                      26

<210> SEQ ID NO 5
<211> LENGTH: 27
```

-continued

```
<212> TYPE: DNA
<213> ORGANISM: RNase L

<400> SEQUENCE: 5
attcgcagcg catcgccttc tatcgcc                                              27
```

MUTANT CELL LINES AND METHODS FOR PRODUCING ENHANCED LEVELS OF RECOMBINANT PROTEINS

CROSS-REFERENCE TO RELATED APPLICATIONS

This application claims priority from U.S. Provisional Application No. 60/099,603, filed Sep. 9, 1998.

This invention was made, at least in part, with government support under United States Public Health Service Grants from the Department of Health and Human Services, National Cancer Institute (CA 44059) and the National Institute of Allergy and Infectious Diseases (AI 34039). The U.S. government has certain rights in the invention.

BACKGROUND OF THE INVENTION

Protein therapeutic agents are among the most important human and animal health products to have emerged from the biotechnology revolution of the 1980's and 1990's. These protein therapeutic agents include interferons, growth factors such as colony stimulating factor and erythropoietin, and monoclonal antibodies.

Many protein therapeutics are produced by a process which involves introducing a nucleic acid which encodes the desired exogenous protein into a living cell, expressing the exogenous protein in the cell, and then recovering the protein, referred to hereinafter as the "recombinant protein" from the system. Although a number of different cell types, including bacteria, yeast, insect cells, and plant cells can be used in this process, there are several advantages to using mammalian cells.

The major advantage to using mammalian cells to produce recombinant proteins is that processing of the proteins is normal. In other words, the proteins which are expressed in mammalian cells typically are glycosylated, phosphorylated and have the signal peptides removed therefrom. As a result, the recombinant protein is more similar to the naturally-occurring protein and, thus, more likely to be biologically active and non-antigenic. In addition, the toxic products that are typically produced in bacteria, yeast, insect cells and plant cells are avoided. Moreover, purification of the recombinant protein is often easier since the processed protein is secreted into the culture medium by mammalian cells. Accordingly, agents such as interferon beta, which is used in treatment of multiple sclerosis, currently are produced in Chinese hamster ovary (CHO)cells.

Unfortunately, high levels of the exogenous protein are not normally produced when mammalian cells are used in the recombinant process. Accordingly, it is desirable to have new methods for enhancing the expression of exogenous proteins in mammalian cells. Immortalized mutant mammalian cell lines which are capable of producing greater amounts of recombinant, exogenous proteins than their corresponding non-mutant mammalian cell lines are also desirable.

SUMMARY OF THE INVENTION

The present invention provides immortalized mutant cell lines that are capable of producing enhanced levels of exogenous, recombinant proteins. The mutant cell lines comprise mammalian somatic cells having a homozygous disruption in the gene which encodes the endoribonuclease known as RNase L and a homygous disruption in the gene which encodes the double-stranded RNA dependent kinase known as PKR. As used herein a "disruption" is a deletion of all or a portion of the RNase L gene or the PKR gene, an addition of one or more nucleotides to the RNase L gene or the PKR gene, a substitution of one or more of the nucleotides in the RNase L gene or the PKR gene, or any combination thereof. Preferably, the disruptions are in a coding exon of the RNase L and PKR genes. As a result of the homozygous disruptions, the mutant cell line, referred to hereinafter as the "double knock-out" or "DKO" cell line lacks biologically active forms of both the RNase L enzyme and the PKR enzyme.

The present invention also provides methods for producing enhanced levels of recombinant proteins, or polypeptides, in mammalian cell systems. In one aspect the method employs cells of the DKO cell line and comprises transfecting the DKO cells with a nucleic acid, or polynucleotide, encoding a desired, exogenous protein, or polypeptide; expressing the exogenous protein in the cell; and isolating the exogenous protein from the system, i.e., from the transfected cells, the culture medium of the transfected cells, or both. Preferably, the DKO cells are also transfected with, i.e., co-transfected with, a nucleic acid encoding the PKR inhibitor, adenovirus VAI RNA.

In another aspect the method employs mutant cells having a homozyous disruption in the RNase L gene alone, referred to hereinafter as "RNase L null" cells. RNase L null cells lack functional RNase L enzyme. The RNase L null cells are transfected with a nucleic acid encoding a desired, exogenous protein. Then the exogenous protein is expressed in the cell and isolated from the system. Preferably, the RNase L cells are co-transfected with a nucleic acid encoding adenovirus VAI RNA, or a nucleic acid encoding a dominant negative PKR, or a combination thereof. The subsequent steps involve expressing the nucleic acids that have been transfected into the RNase L null cells and isolating or purifying the exogenous protein from the system.

In another aspect the methods employ mutant cells having a homozygous disruption in the PKR gene, hereinafter referred to as "PKR null" cells. PKR null cells lack a functional PKR enzyme. In one embodiment, the method comprises co-transfecting the PKR null cells with a nucleic acid encoding adenovirus VAI RNA and with a nucleic acid encoding a desired, exogenous protein, expressing the exogenous protein in the cell, and isolating the exogenous protein from the system. In another embodiment, the method comprises co-transfecting the PKR null cells with a nucleic acid encoding a dominant negative RNase L and with a nucleic acid encoding a desired, exogenous protein; expressing the dominant negative RNase L and the desired, exogenous protein in the cell; and isolating the exogenous protein from the system. Preferably, the PKR null cells are transfected with a nucleic acid encoding adenovirus VAI RNA and a nucleic acid encoding a dominant negative RNase L, as well as with the nucleic acid encoding the exogenous protein.

In another aspect, the method comprises cotransfecting mammalian cells with a nucleic acid encoding the desired exogenous protein and a nucleic acid encoding a dominant negative RNase L or a dominant negative PKR. Preferably, the mammalian cells are cotransfected with both a nucleic acid encoding a dominant negative PKR and a nucleic acid encoding a dominant negative RNase L. More preferably, the mammalian cells are also transfected with a nucleic acid encoding adenovirus VAI RNA. The subsequent steps involve expressing the nucleic acids that have been transfected into the RNase L null cells and isolating the exogenous protein from the system.

The present invention also relates to methods of making the double knock-out cell line.

BRIEF DESCRIPTION OF THE FIGURES

FIG. 13 shows the nucleotide sequence, SEQ ID NO:1 of a cDNA encoding mouse RNase L, and the amino acid sequence, SEQ ID NO:2, of mouse RNase L.

DETAILED DESCRIPTION OF THE INVENTION

Figure 1:
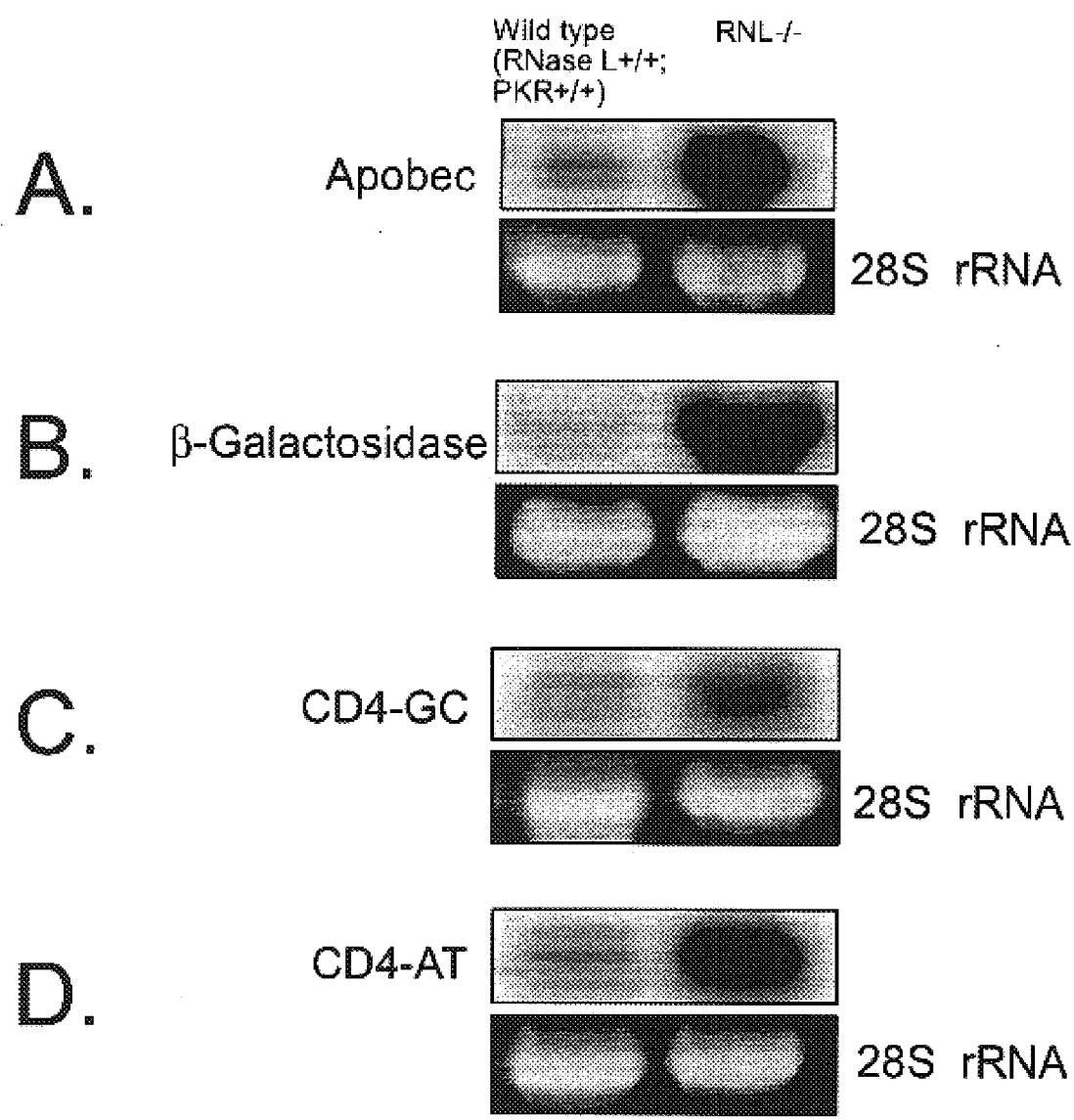
FIG. 1. Enhanced levels of RNAs are expressed from different genes transfected into RNase L$^{-/-}$ cells. Induction of (A) apobec, (B) β-galactosidase, (C) CD4-GC and (D) CD4-AT mRNAs in wild type (RNase L$^{+/+}$; PKR$^{+/+}$) and RNase L$^{-/-}$ cells. Total cellular RNA was isolated at 18 h after transient transfection with 2 μg of each cDNA separately; and with 30 μg loaded per lane. Differences in RNA loading were examined by comparing with 28S ribosomal RNA ethidium bromide staining (lower panels).

In accordance with the present invention, methodologies and mammalian cell lines useful for the large scale production of recombinant proteins are provided. In one aspect, the methods employ mammalian cells in which the endoribonuclease RNase L has either been ablated or inhibited. RNase L, which is found in basal levels in most mammalian cells is an unusual endoribonuclease that requires allosteric effectors to catalyze the hydrolysis of single-stranded RNA. In another aspect the method employs cells in which both RNase L and the double-stranded RNA dependent kinase known as PKR have been ablated or inhibited. In another aspect, the methods employ mutant mammalian cells, preferably mutant mouse cells, lacking functional RNase L, functional PKR, or both and comprising or containing adenovirus VAI RNA. In accordance with the present invention, it has been discovered that methods which involve ablation or inhibition of both PKR and RNase L in mammalian cells greatly increases the expression of exogenous proteins in such cells as compared to mammalian cells having functional RNase L and functional PKR enzymes. Accordingly, the present methods are useful for producing enhanced levels of protein therapeutics in mammalian cells.

The Mutant Cell Line

In accordance with the present invention a novel mammalian cell line for producing high levels of a recombinant exogenous protein has been discovered. The cell line, which preferably is an immortalized cell line, is made up of somatic cells having a homozygous disruption in the gene which encodes the endoribonuclease RNase L and a homozygous disruption in the gene which encodes the double-stranded RNA dependent kinase known as PKR. As used herein the "disruptions" are a deletion of all or a portion of the RNase L gene and the PKR gene, an addition of one or more nucleotides to the RNase L gene and the PKR gene, a substitution of one or more of the nucleotides in the RNase L gene and the PKR gene, or any combination thereof. Preferably, the disruptions are in a coding exon of the RNase L and PKR genes. As a result of the homozygous disruptions, the mutant cell line lacks functional RNase L and PKR enzymes.

The DKO cell line is obtained by isolating somatic cells from a mutant non-human mammal comprising a homozygous disruption in both the RNase L gene and the PKR gene thereof. For example fibroblasts can be obtained from such animals and immortalized using conventional methods. In one embodiment, the mutant cell line is a mouse fibroblast cell line Such cell line may be produced by intercrossing mice which are heterozygous for the RNase L gene with mice which are heterozygous for the PKR gene and isolating mouse embryo fibroblasts from embryos having the genotype RNase $L^{-/-}$ PKR$^{-/-}$. Methods for intercrossing mice, isolating fibroblasts from the resulting embryos, and immortalizing such primary fibroblasts are well known in the art.

Methods for preparing mice having a heterozygous disruption in the PKR gene are described in Yang, Y. L. et al. "Deficient signaling in mice devoid of double-stranded RNA-dependent protein kinase.", EMBO J. 14, 6095–6106 (1995), which is specifically incorporated herein by reference. Methods for preparing mice having a heterozygous disruption in the RNase L gene or a homozygous disruption in the RNase L gene are described in Zhou, A. et al. "Interferon action and apoptosis are defective in mice devoid of 2',5'-oligoadenylate-dependent RNase L." EMBO J. 16, 6355–6363 (1997) which is specifically incorporated herein by reference. Such mutant mice are produced by introducing a transgene into their germline. As used herein, the "transgene" is a variant of the RNase L gene. The transgene comprises a deletion of all or a portion of the RNase L gene or, an addition of a heterologous nucleic acid sequence to the wild-type RNase L gene, or a substitution of one or more base pairs in the RNase L gene. Preferably, the heterologous nucleic acid sequence is a marker sequence. More preferably, the heterologous nucleic acid sequence comprises a marker sequence that is inserted in the reverse orientation as compared to the coding sequence of the RNase L gene. As used herein the term "marker sequence" refers to a nucleic acid sequence that is used (1) to disrupt expression of the RNase L gene and (2) to identify those cells that have incorporated the transgene into the genome thereof. Suitable marker sequences are those that encode an assayable or selectable product and include, for example, antibiotic resistance genes or genes that encode an assayable enzyme not typically found in the cell. Where the marker sequence encodes a protein, the marker sequence will also typically contain a promoter that regulates its expression. The methods for preparing such DNA constructs are well-known in the art and, typically, employ genomic libraries and standard recombinant techniques.

Preferably, the disruption is in coding exon 1, coding exon 2, coding exon 3 or coding exon 4 of an RNase L gene, more preferably coding exon 1 of the mouse RNase L gene. The nucleotide sequence of a cDNA which encodes mouse RNase L and the amino acid sequence of the mouse RNase L enzyme are shown in FIG. 13. Coding exon 1 encodes amino acids 1 to 491; coding exon 2 encodes amino acids 492–519, and coding exon 3 encodes amino acids 520 through 611 of the wild-type mouse RNase L enzyme.

METHOD FOR PRODUCING HIGH LEVELS OF RECOMBINANT PROTEINS

In one aspect the methods of the present invention comprise transfecting a mutant mammalian cell having a homozygous disruption in the RNase L gene thereof, or in the PKR gene thereof, or, preferably, in both the RNase L and PKR genes thereof with a nucleic acid having a sequence which encodes a desired exogenous protein, expressing the protein, and then isolating the exogenous protein that has been synthesized in the mutant cell, i.e., the recombinant protein. As used herein "endogenous" refers to proteins that are encoded by one of the genes that exist in the natural or unmodified genome of the mammal from which the mutant mammalian cell was derived. As used herein "exogenous" refers to proteins encoded by a nucleic acid which is introduced into the cell using recombinant technology procedures, i.e. the transfected nucleic acid. The amino acid sequence of the exogenous protein may identical to the amino acid sequence of an endogenous protein. Preferably, the amino acid sequence of the exogenous protein is different from the amino acid sequences of the endogenous proteins of the cell. Somatic cells having a homozygous disruption in both the RNase L gene and the PKR gene, i.e. DKO cells, are prepared as described above. Somatic cells having a homozygous disruption of the RNase L gene alone are prepared as described in Zhou et al. Somatic cells having a homozygous disruption of the PKR gene alone are prepared as described in Yang et al.

Preferably, the mutant cells also comprise adenovirus VAI RNA. Such mutant cells are made by transiently transfecting or stably transfecting the mutant cell with a nucleic acid having a sequence which encodes adenovirus VAI RNA. A vector suitable for transfecting the mutant cell with a nucleic acid encoding adenovirus VAI RNA is available from Promega and is sold under the product name pAdVAntage. The pAdVAntage vector also encodes VAII RNA of adenovirus.

In another aspect, the method comprises cotransfecting a mammalian cell with a nucleic acid encoding the desired protein, hereinafter referred to as the "first nucleic acid" and a nucleic acid having a sequence which encodes an inhibitor of PKR, referred to hereinafter as the "second nucleic acid", or a nucleic acid encoding an inhibitor of RNase L, referred to hereinafter as the "third nucleic acid", or with both the second nucleic acid and the third nucleic acid. Preferably, the cells are transfected with a nucleic acid encoding adenovirus VA 1 RNA. The cells are cultured under conditions suitable for expressing the desired, exogenous protein, the PKR inhibitor, or the RNase L inhibitor, and, if necessary, the adenovirus VA 1, RNA, and then the recombinant protein is isolated from the system.

Examples of second nucleic acids are nucleic acids which encode a dominant negative PKR and nucleic acids which encode adenovirus VA 1 RNA. As used herein a "dominant negative protein" is a mutant form of a protein which has the property of inhibiting the function of the endogenous, wild type form of the protein which corresponds to the mutant protein. Typically, dominant negative proteins have amino acid substitutions or are truncated forms of the wild type protein. One example of a dominant negative RNase L, ZB1, is described in Hassel, B. A., Zhou, A., Sotomayor, C., Maran, A. & Silverman, R. H., "A dominant negative mutant of 2–5A-dependent RNase suppresses antiproliferative and antiviral effects of interferon.", EMBO J. 12, 3297–3304 (1993), which is specifically incorporated herein by reference. ZB1 is derived from murine RNase L, but lacks the 89 carboxy terminal amino acids. ZB1 protein binds the activator of RNase L, 2–5A, but lacks ribonuclease activity and is capable of inhibiting the function of wild type RNase L. An example of a dominant negative of PKR is PKR (Lys296 Arg). PKR (Lys296Arg) is described in Katze M G, Wambach M, Wong M L, Garfinkel M, Meurs E, Chong K, Williams B R, Hovanessian A G, Barber G N, "Functional expression and RNA binding analysis of the interferon-induced, double-stranded RNA-activated, 68,000-Mr protein kinase in a cell-free system.", Mol Cell Biol 11: 11,5497–505, November, 1991, which is specifically incorporated herein by reference. PKR (Lys296Arg) contains a single amino acid substitution in the protein kinase domain II which is responsible for binding the alpha and beta phosphoryl groups of ATP and is required for protein kinase activity.

Cells employed in such methods include mutant mammalian cells such as for example RNase null cells and PKR null cells, as well as wild-type mammalian cells such as for example, CHO cells. In those instances where RNase null cells are used, it is preferred that the cells be co transfected with a nucleic acid encoding the desired exogenous protein and with a nucleic acid encoding a dominant negative PKR. More preferably, such cells are also transfected with a nucleic acid encoding adenovirus VA I RNA. In those cases where PKR null cells are used, it is preferred that the cells be transfected with a nucleic acid encoding the desired exogenous protein and with a nucleic acid encoding a dominant negative RNase L. More preferably, such cells are also transfected with a nucleic acid encoding VAI RNA. In those cases where wild-type mammalian cells are used, the cells are co-transfected with a first nucleic acid encoding the desired endogenous protein and a second nucleic acid encoding a dominant negative mutant form of PKR or a dominant negative form of RNase L. Preferably, the cells are co-transfected with the first nucleic acid and one of the following combinations: (1) a nucleic acid encoding a dominant negative mutant form of PKR and a nucleic acid encoding VAI RNA, (2) a nucleic aid encoding a dominant negative mutant form of PKR and a nucleic acid encoding a dominant negative RNase L, or (3) a nucleic acid encoding a dominant negative RNase L and a nucleic acid encoding adenovirus VAI RNA. More preferably, the wild-type cells are co-transfected with the first nucleic acid, a nucleic acid encoding a dominant negative PKR, a nucleic acid encoding a dominant negative RNase L, and a nucleic acid encoding adenovirus VAI RNA.

Promoters for the Nucleic Acids

The first nucleic acid, second nucleic acid, and third nucleic acid are operatively linked to a promoter, preferably a constitutive promoter, which promotes expression of the nucleic acids. Useful promoters include the CMV promoter, the SV40 promoter, and the beta actin promoter. Preferably, the first nucleic acid, second nucleic acid and third nucleic acid are incorporated into a vector comprising the promoter, such as for example a plasmid. Plasmids comprising such promoters are available commercially. Vectors for transfection of the nucleic acids into the mammalian cells, preferably, also include transcription initiation, termination and enhancer sequences, as well as sequences that enhance translation efficiency, such as the Kozak sequence. Preferably, the vector also includes a marker gene for selecting for the presence of the vector in the cell.

Although the nucleic acids may be contained within the same vector, it is preferred that the first nucleic acid, the second nucleic acid, and the third nucleic acid each be on separate vectors. In such case, the cell may be transfected with the second nucleic acid, the third nucleic acid, or both prior to transfection with the first nucleic acid or concurrently with the first nucleic acid. Introduction of the vector or vectors into the mammalian cell can be accomplished using a variety of methods well known in the art, such as for example, retrovirus-mediated transduction, microinjection, calcium phosphate treatment, lipid-mediated transfection or electroporation.

Following introduction of the vector into the cell, the transfected cells are incubated under conditions which are suitable for expression of the exogenous protein. Thereafter, the recombinant protein, i.e., the exogenous protein, is isolated from the transfected cells and, if secreted, from the culture medium of the transfected cells using conventional procedures. Following expression of the exogenous protein and growth of the transfected host cell to an appropriate cell density, the cells are harvested by centrifugation, disrupted by physical or chemical means, and the resulting crude extract retained for further purification of the recombinant protein or polypeptide.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, and high performance liquid chromatography (HPLC), and affinity chromatography may be used to isolate the recombinant protein.

The following non-limiting examples are presented to further illustrate the present invention.

EXAMPLE 1

Double Mutant Cell Lines

Mice comprising non-embryonic cells having a heterozygous disruption in the RNase L gene thereof were obtained by employing the methods described in Zhou, . et al. Interferon action and apoptosis are defective in mice devoid of 2',5'-oligoadenylate-dependent RNase L. EMBO J. 16, 6355–6363 (1997), which is specifically incorporated herein by reference. Mice comprising non-embryonic cells having a heterozygous disruption in the PKR gene thereof were obtained by employing the methods described in Yang, Y. L. et al. Deficient signaling in mice devoid of double-stranded RNA-dependent protein kinase., EMBO J. 14, 6095–6106 (1995)(8), which is specifically incorporated herein by reference. Embryonic fibroblasts containing a homozygous disruption in the both the RNase L gene and the PKR gene were obtained by intercrossing mice which were heterozygous for the RNase L gene and the PKR gene with mice which were heterozygous for the PKR gene and the RNase L gene and isolating mouse embryo fibroblasts (MEFs) from the resulting embryos at day 16.5 post-coitum. Individual sibling embryos were removed, while maintaining sterility, to tissue culture dishes containing PBS. The embryos were minced and pieces of tissue were removed for genotyping by Southern blot analysis. The remaining tissue was incubated at 4° C. for 16 h with 0.05% trypsin and 0.53 mM EDTA. The excess trypsin solution was then aspirated and discarded and the tissue was incubated at 37° C. for 30 minutes. Two volumes of DMEM containing 10% FBS was added followed by vigorous pipetting to break up the tissue into cells. The cells were then cultured in fresh DMEM/10% FBS.

The presence or absence of homozygous disruptions of both the RNase L gene and the PKR gene in the cells derived from individual embryos was determined by PCR and Southern blot assays, respectively, of DNA extracted from such cells. Southern blots for the RNase L gene were determined on DNA digested with XbaI probed with a $^{32}$P-labeled HindIII fragment of the murine RNase L gene. Analysis of the PKR locus was performed by PCR using a common upstream primer, PC1 (5'-GTTTGGCTATTTCTCTGTGTTCATTGGA-3'), SEQ ID NO. 3, paired either with PKR-X2 (5'-GTAATGGCTACTCCGTGCATCTGGGC-3'), SEQ ID NO: 4 to detect the wildtype PKR allele, or with NEO-P3 (5'-ATTCGCAGCGCATCGCCTTCTATCGCC-3'), SEQ ID NO: 5, to detect the targeted PKR mutant allele. RNase L was assayed as described in Nolan-Sorden, N. L., Lesiak, K., Bayard, B., Torrence, P. F. & Silverman, R. H., "Photochemical crosslinking in oligonucleotide-protein complexes between a bromine-substituted 2–5A analog and 2–5A-dependent RNase by ultraviolet lamp or laser.", *Anal. Biochem.* 184, 298–304 (1990).

Protein extracted from the cells was assayed by Western blots. Antibodies used were polyclonal anti-murine PKR antibody raised in PKR-1- mice at 1:500, rat monoclonal anti-43 kDa 2–5A synthetase (6810) antibody[9] at 1:500 and anti-actin antibody (Boehringer Mannheim) at 1:6000. Primary antibodies were detected using anti-mouse IgG-HRP or anti-rabbit IgG-HRP (Gibco/BRL) at 1:5000 with enhanced chemiluminescence, ECL (Amersham). Analysis of IFN-induction of proteins was by treating cells with 2,000 units per ml of IFNα for 18 h (20). The amounts of cell extracts was 200 μg of protein per lane.

The results indicated that approximately 1/16 of the embryos provided fibroblasts having the PKR$^{-/-}$: RNase L$^{-/-}$ genotype. Immortalized double mutant cell lines, hereinafter referred to as DKO cells, were derived by continuous culturing for 10 to 14 passages of these cells.

EXAMPLE 2

Producing Enhanced Levels of Exogenous Recombinant Proteins in DKO cells.

Primary cultured MEFs that lack both RNase L and PKR prepared as described in EXAMPLE 1 were maintained in Dulbecco's modified medium (DMEM) supplemented with 10% heat-inactivated fetal bovine serum (FBS) at 37° C. in a humidified 5% $CO_2$ atmosphere. Fibroblasts were seeded 16 h before transfection at a density of $1 \times 10^6$ to $1.3 \times 10^6$ cells per 100 mm-diameter dish or $1 \times 10^5$ to $1.3 \times 10^5$ per well in 6 well plate with same medium as above and incubated in 5% $CO^2$ at 37° C. At 16 h after plating, cells were transfected with pSV β-galactosidase vector (4 μg) containing β-galactosidase cDNA (Promega), using lipofectamine PLUS transfection reagent (GIBCO-BRL) according to manufacturer's protocol.

The expression of the exogenous protein was assayed by measuring β-galactosidase activity in the transfected cells according manufacturer's protocol (Promega). After washing the cells with PBS, 800 μl of lysis buffer (0.1 M $K_2PO_4$ pH 7.8, 0.2% Triton-100, 1 mM DTT) was added. Cell extracts were harvested by scraping and after centrifuging for 3 mini, 50 μl of the cell extracts (diluted 1:8 with lysis buffer) was added to 400 μl of Assay 2×Buffer (120 mM $Na_2HPO_4$; 80 mM $NaH_2PO_4$; 2 mM $MgCl_2$; 100 mM β-mercapoethanol; 1.33 mg/ml ONPG). The reaction was incubated 30–45 minutes at 37° C., and absorbance at 420 nm was determined in a spectrophotometer. The pellet was solubilized with 300 μl of 0.1 M NaOH and neutralized before to determine protein concentration by Bradford protein-dye binding methods (BIORAD) using bovine serum albumin as standard. Negative controls were done on untransfected cells. Data are averages from three separate experiments, each in done in duplicate. β-galactosidase activities were normalized for protein concentrations.

Figure 10:
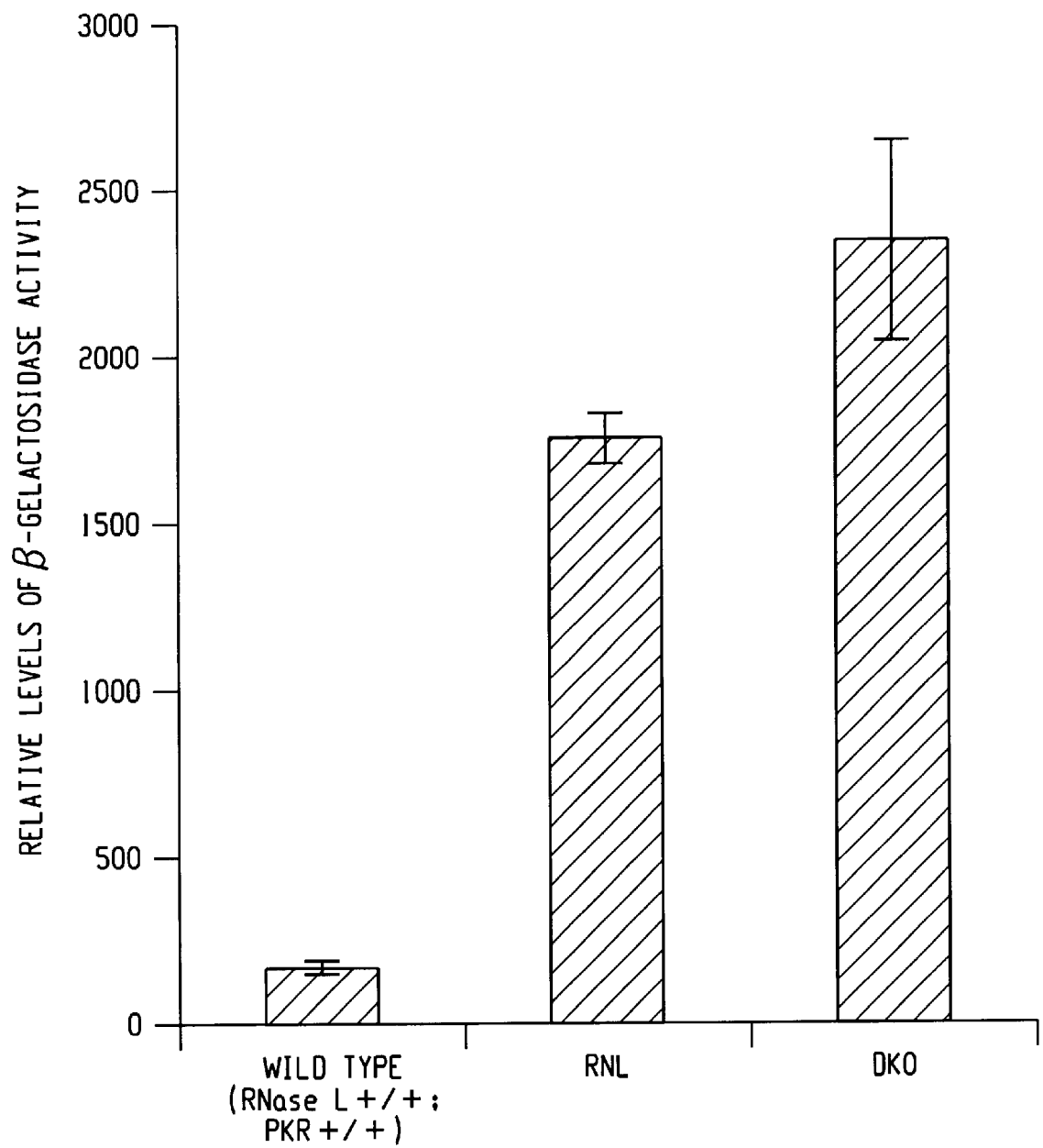
FIG. 10. Immortalized RNase L$^{-/-}$; PKR$^{-/-}$ cells overexpress β-galactosidase. The double knockout (DKO), RNase L$^{-/-}$; PKR$^{-/-}$ cells were transfected with 4 μg of pSV-β-galactosidase and β-galactosidase assay was performed 18 h after transient transfection. β-galactosidase activity was normalized against protein concentration. Results are reported as relative absorbance units per $10^6$ cells. Values were averages of 5 independent transfections and were derived from sets of duplicate transfection. Some error bars were too small to appear above the graph.
Figure 11:
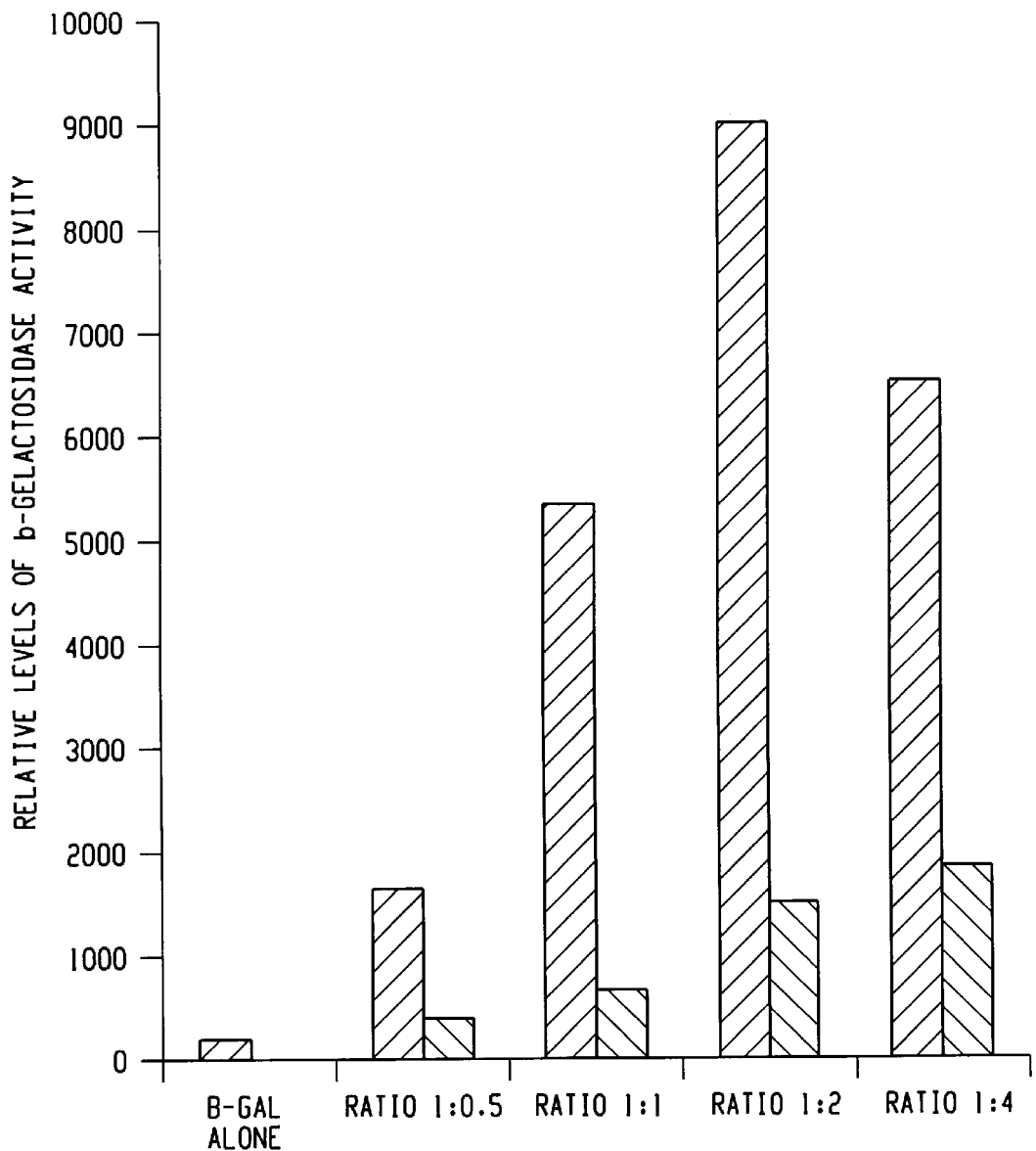
FIG. 11. VAI RNA enhances β-galactosidase expression in DKO cells. DKO cells were transiently cotransfected with 2 μg of pSV-β-galactosidase and different amounts of pAdVAntage or different amounts of pBR322. After 18 h, β-galactosidase activity was measured.

As shown in FIG. 10, 10-fold and 13-fold-fold overexpression of β-galactosidase activity was obtained in primary RNase$^{-/-}$ cells and in DKO cells, respectively, as compared to control fibroblasts.

EXAMPLE 3

Producing High Levels of Recombinant Exogenous Proteins in RNase L$^{-/-}$ cells.

RNase $^{-/-}$ cells were prepared as described in Zhou, A. et al. Interferon action and apoptosis are defective in mice devoid of 2',5'-oligoadenylate-dependent RNase L. EMBO J. 16, 6355–6363 (1997) which is specifically incorporated herein by reference. Immortalized RNase L$^{-/-}$ cells were derived by continuous culturing as described above. The RNase L$^{-/-}$ cells were transfected with pSV β-galactosidase vector (4 ptg), 2 μg pCR3.1/APOBEC vector contain full length of APOBEC cDNA, or 2 μg of pRcCMV/CD4 GC, or 2 μg of pRcCMV/CD4 AT. Total cellular RNA was isolated from the transfected cells with RNAzol according manufacturer's protocol (CNNA/BIOTEX). RNAs were separated in 1.2% agarose-formaldehyde gel, and transferred into Nylon transfer membrane (Amersham) for 18–20 hours. The membranes were hybridized with $^{32}$P-dCTP labeled probe prepared by random priming using rediprime DNA labeling system (Amersham).

As shown in FIG. 1, exogenously expressed mRNAs accumulated to high levels in the RNase L$^{-/-}$ cells, which lack functional RNase L. Such cells overexpressed a variety of different types of mRNAs, expressed from different promoters. For example, RNase L$^{-/-}$ cells transfected with apobec cDNA, encoding an RNA editing enzyme, expressed from a CMV promoter, produced about 15-fold higher levels of mRNA than in matched RNase L$^{+/+}$ cells (FIG. 1A). The β-galactosidase cDNA in a plasmid driven by an SV40 promoter was also overexpressed in RNase L$^{-/-}$ cells. (FIG. 1B). Exogenous transcripts encoding the cell surface antigen CD4 fused to an instability sequences (ARE) from the 3'-untranslated region of the GM-CSF mRNA transcribed from a CMV promoter accumulated to higher levels in RNase L$^{-/-}$ than in RNase L$^{+/+}$ cells (FIG. 1D). CD4 transcripts fused to mutated GM-CSF 3' sequence, in which A's and U's in the ARE were mutated to G's and C's, were also expressed to higher levels in RNase L$^{-/-}$ than in RNase L$^{+/+}$ cells (FIG. 1C).

Figure 2:
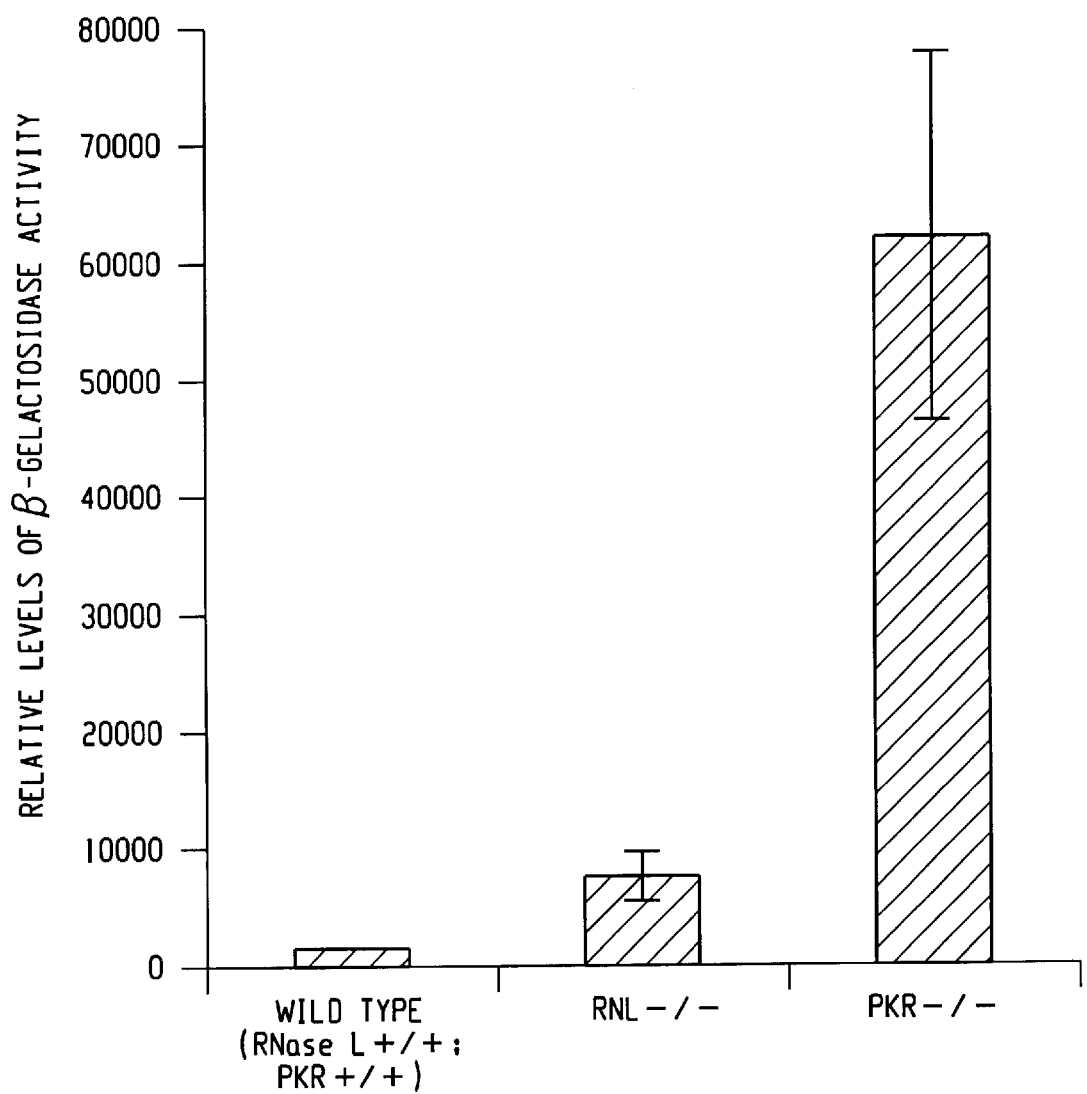
FIG. 2. β-galactosidase is overexpressed RNase L(RNL)$^{-/-}$ and PKR$^{-/-}$ cells. Cells were transfected with 4 μg of pSV-β-galactosidase vector and the β-galactosidase assay was performed 18 h after transient transfection. β-galactosidase activity reported represents the relative absorbance units per $10^6$ cells. Values are an average of 3 independent transfections and were derived from sets of duplicate transfections. Some error bars were too small to appear on the graph.

To determine if the enhanced levels of plasmid derived mRNA observed in immortalized RNase L$^{-/-}$MEF cells resulted in increased production of protein, expression of β-galactosidase activity from a transfected cDNA under control of an SV40 promoter was measured (FIG. 2). The expression of B-galactosidase was determined as described above in example 1. After transient transfections, a 5-fold higher level of β-galactosidase activity was observed in RNase L$^{-/-}$MEF cells as compared to the wild type cells.

To establish if these results could be extended to other genes expressed from different promoters, the RNase null MEF cell lines were transiently transfected with luciferase cDNA under control of either a CMV promoter or an SV40 early promoter. To determine if levels of luciferase expression was enhanced in these cells, luciferase activity was assayed following manufacturer's protocol (PROMEGA). The cells were rinsed with phosphate buffered saline (PBS) and lysed with 500 µl of 1×lysis buffer, scraped and centrifuged for 2 min in a microfuge at 12,000 g. Supernatants were recovered for luciferase assay, 2 µl of lysate were mixed with 50 µl of the luciferase substrate solution and the emitted fluorescence was immediately measured. As a negative control, extract from untransfected cells was used. The pellets were solubilized with 50 µl of 0.1 M NaOH and neutralized before determining protein concentrations by Bradford protein-dye binding methods (BIORAD) using bovine serum albumin as a standard. Data presented are averages of duplicated experiments.

Figure 3:
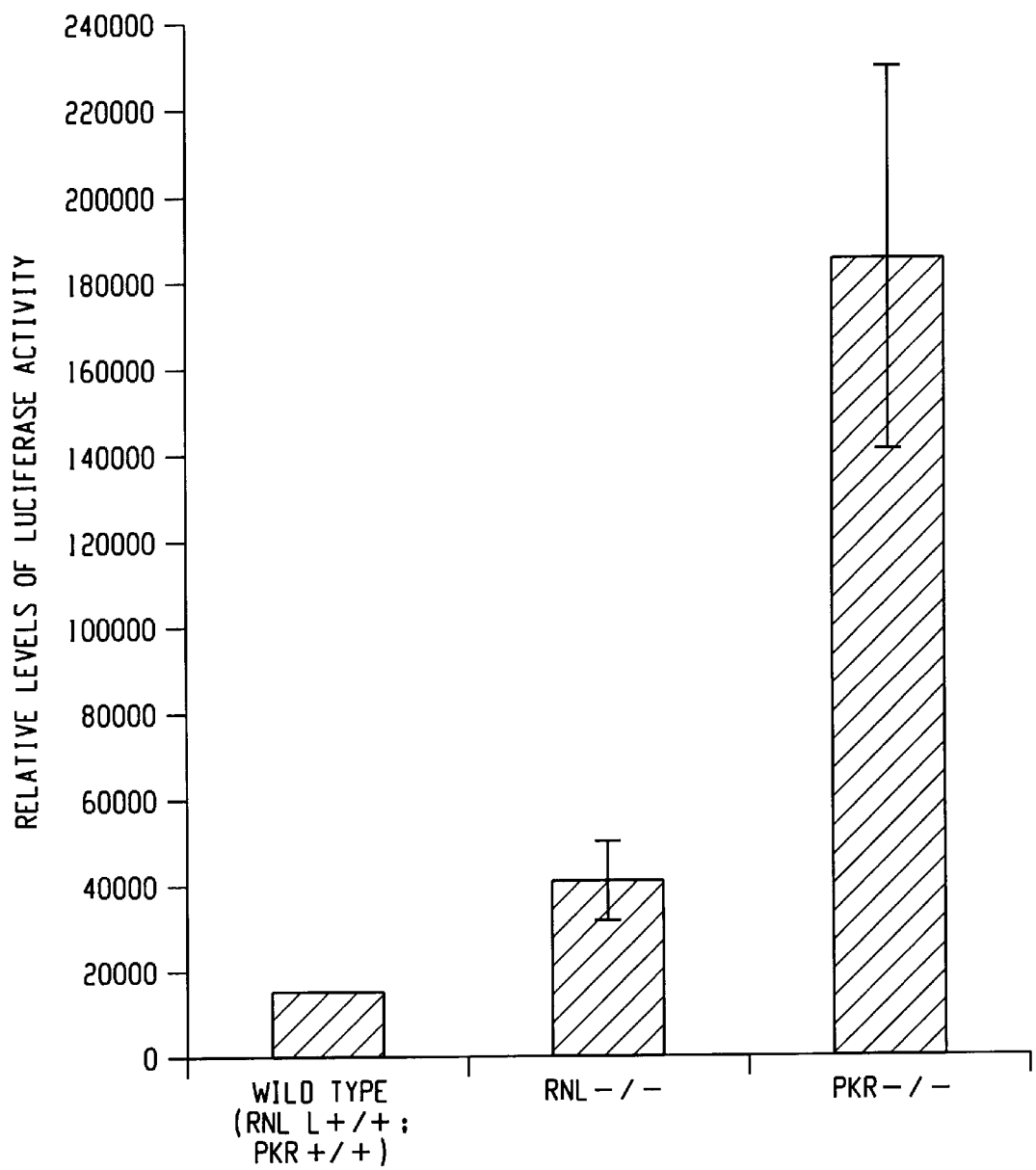
FIG. 3. A luciferase gene driven by a CMV promoter is overexpressed in RNase L$^{-/-}$ and PKR$^{-/-}$ cells. Cells were transfected as described in Materials and Methods and after 18 h luciferase activity was assayed. Luciferase activity reported represents the relative luminescence units per $10^6$ cells. Values were average of 6 independent transfections and were derived from averages of duplicate transfections. Some error bars were too small to appear on the graph.
Figure 4:
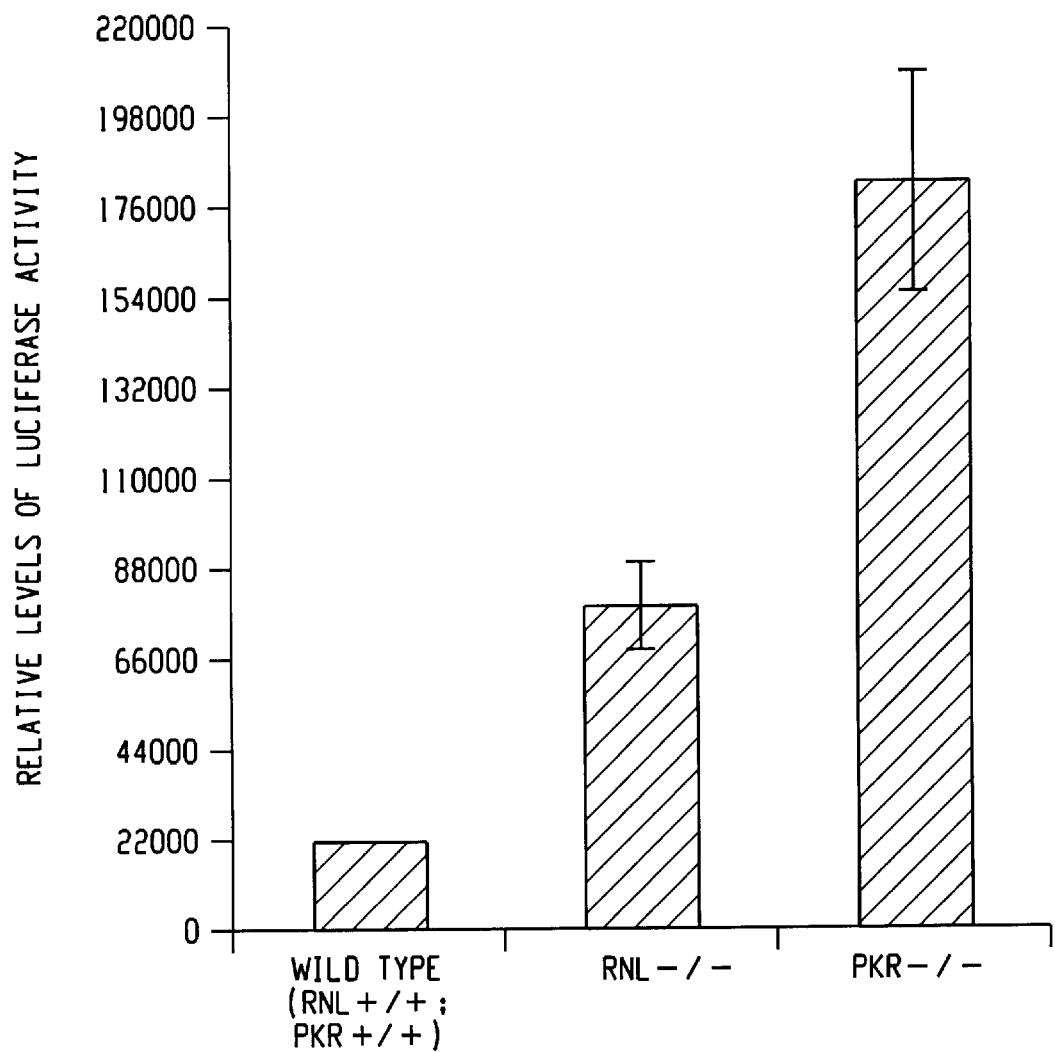
FIG. 4. A luciferase gene driven by an SV40 promoter is overexpressed in RNase L$^{-/-}$ and PKR$^{-/-}$ cells. Cells were transfected as described in Materials and Methods and after 18 h luciferase activity was assayed. Luciferase activity reported represents the relative luminescence units per $10^6$ cells. Values are averages of 6 independent transfections and were derived from sets of duplicate transfection.

As shown in FIGS. 3 and 4, respectively, luceriferase activity was 3.6-fold and 2.6-fold higher in the RNase $L^{-/-}$ than in the RNase $L^{+/+}$ cells when expressed from the CMV and SV40 promoters, respectively. Therefore, the choice of promoter did not significantly affect the results.

EXAMPLE 4

Producing High Levels of Recombinant Exogenous Proteins in $PKR^{-/-}$ cells.

$PKR^{-/-}$ cells were obtained from $PKR^{-/-}$ mice as described in Yang et al. Cells were transiently transfected as described above in example 3 with plasmids comprising DNA encoding β-galactosidase and luciferase and the activities of these enzymes assayed as described in example 3. As shown in FIG. 2, a 39-fold higher level of β-galactosidase activity was observed in $PKR^{-/-}$ MEF cells as compared to the wild type cells. As shown in FIGS. 3 and 4, luciferase activity was 8.3-fold and 11.6-fold higher in the $PKR^{-/-}$ than in the $PKR^{+/+}$ cells when expressed from the CMV and SV40 promoters, respectively. That both β-galactosidase and luciferase were overexpressed in cells lacking RNase L or PKR indicates that different exogenously expressed proteins can be produced to high levels in each of these cell types

EXAMPLE 5

Producing High Levels of Recombinant Exogenous Proteins in RNase $L^{-/-}$ Cells by Co-transfection with a DNA Encoding a Dominant Negative PKR.

RNase $L^{-/-}$ MEF cells prepared as described above were co-transfected with pSV β-galactosidase vector and with pRcCMV/PKRm vector encoding a mutant PKR, lysine-to-arginine at position 296, which lacks kinase activity. The method for preparing pRcCMV/PKRm vector is described in Katze M G, Wambach M, Wong M L, Garfinkel M, Meurs E, Chong K, Williams B R, Hovanessian A G, Barber G N, Functional expression and RNA binding analysis of the interferon-induced, double-stranded RNA-activated, 68,000-Mr protein kinase in a cell-free system., Mol Cell Biol 11: 11,5497–505, November, 1991, which is specifically incorporated herein by reference.

Figure 5:
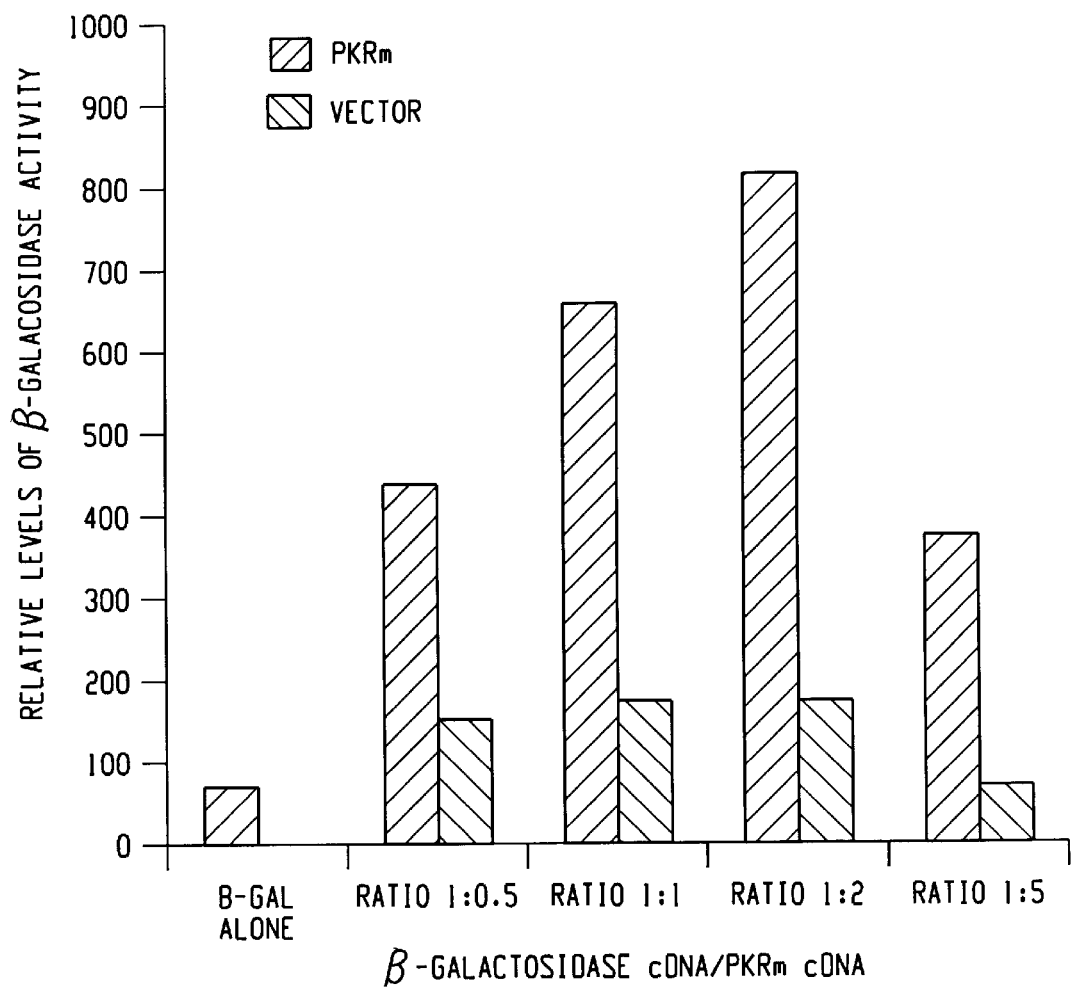
FIG. 5. A dominant negative lyS$_{296}$ to arg mutant PKR, PKRm, greatly stimulates expression of β-galactosidase in RNase L$^{-/-}$ cells. RNase L$^{-/-}$ cells were transiently co-transfected with 2 μg of pSV-β-galactosidase and different amount of pRcCMV/PKRm or pRcCMV. After 18 h β-galactosidase activity was measured. β-galactosidase activity represents values per $10^6$ cells. Values are averages of an experiment performed in duplicate.
Figure 6:
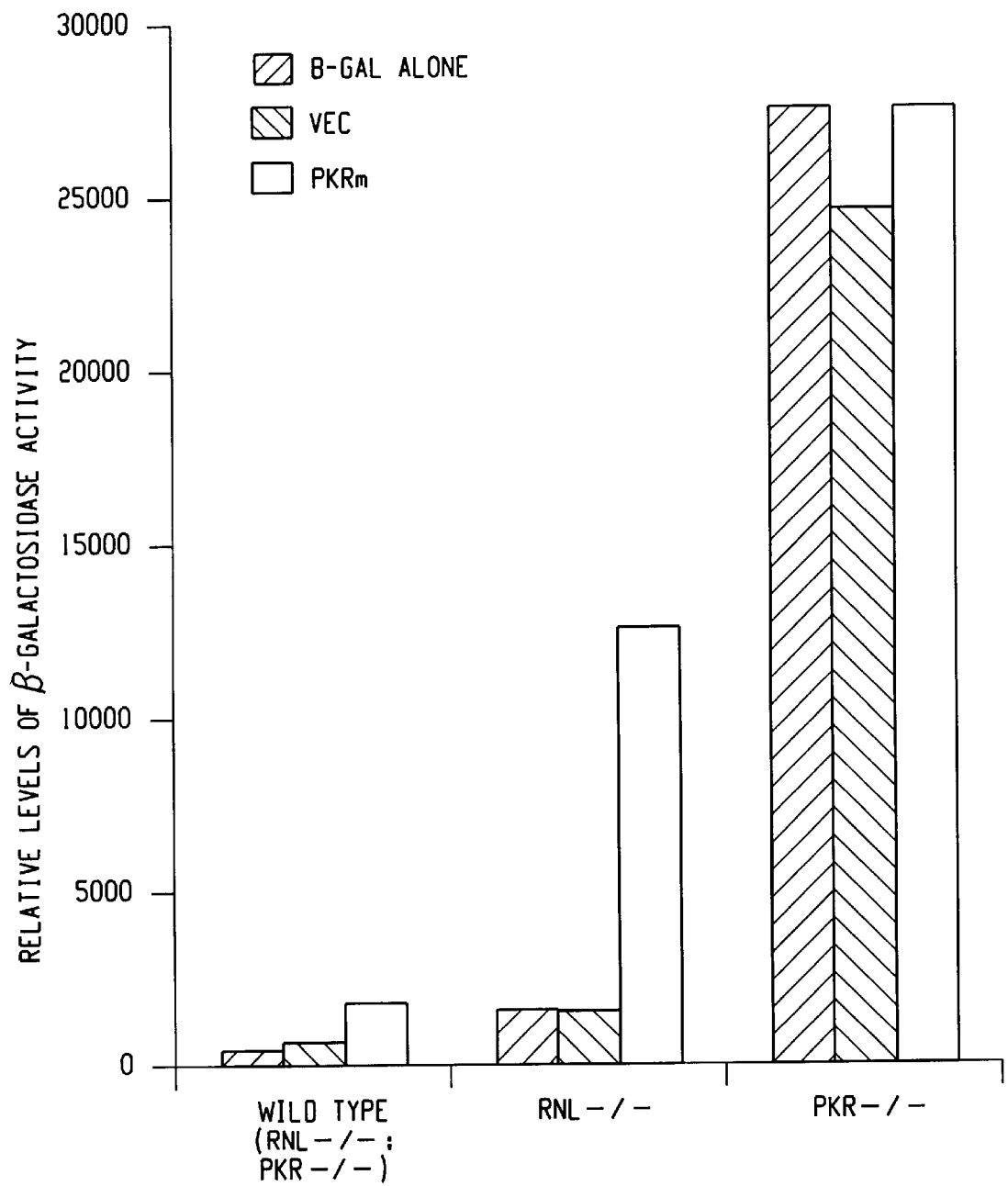
FIG. 6. PKRm enhances expression of β-galactosidase in wild type and RNase L$^{-/-}$ cells but not in PKR$^{-/-}$ cells. Cell were transiently co-transfected with 4 μg of pSV-β-galactosidase and 4 μg of pRcCMV/PKRm or 4 μg of pRcCMV separately. After 18 h, β-galactosidase activity was measured. β-galactosidase represents values per $10^6$ cells. Values are averages from 2 experiments each performed in duplicate. Data are reported as relative absorbance units.

Galactosidase activity was measured as described in Example 1. As shown in FIG. 5, levels of galactosidase activity were increased about 12-fold compared with transfections in the absence of the mutant PKR cDNA. The vector control had a much smaller effect on galactosidase activity. When the mutant PKR cDNA was co-transfected with β-galactosidase cDNA into the different cell types, it was apparent that enhancement in expression was obtained in the wild type and RNase $L^{-/-}$ cells, but not in the $PKR^{-/-}$ cells (FIG. 6). The greatest level of expression was obtained in the $PKR^{-/-}$ cells.

EXAMPLE 6

Producing High levels of Recombinant Exogenous Proteins in $PKR^{-/-}$ Cells by Co-Transfection with a DNA encoding a Dominant Nepative RNase L $PKR^{-/-}$ MEF cells prepared as described above in Example 4 were co-transfected with 2 µg pSV β-galactosidase vector and different concentration of pCDNA/ZB1 vector containing RNase L ZB1 cDNA which encodes a truncated version of RNase L that lacks ribonuclease activity. The method for preparing the pcDNA/ZB1 vector is described in Hassel, B. A., Zhou, A., Sotomayor, C., Maran, A. & Silverman, R. H. "A dominant negative mutant of 2–5A-dependent RNase suppresses antiproliferative and antiviral effects of interferon." *EMBO J.* 12, 3297–3304 (1993), which is specifically incorporated herein by reference.

Figure 9:
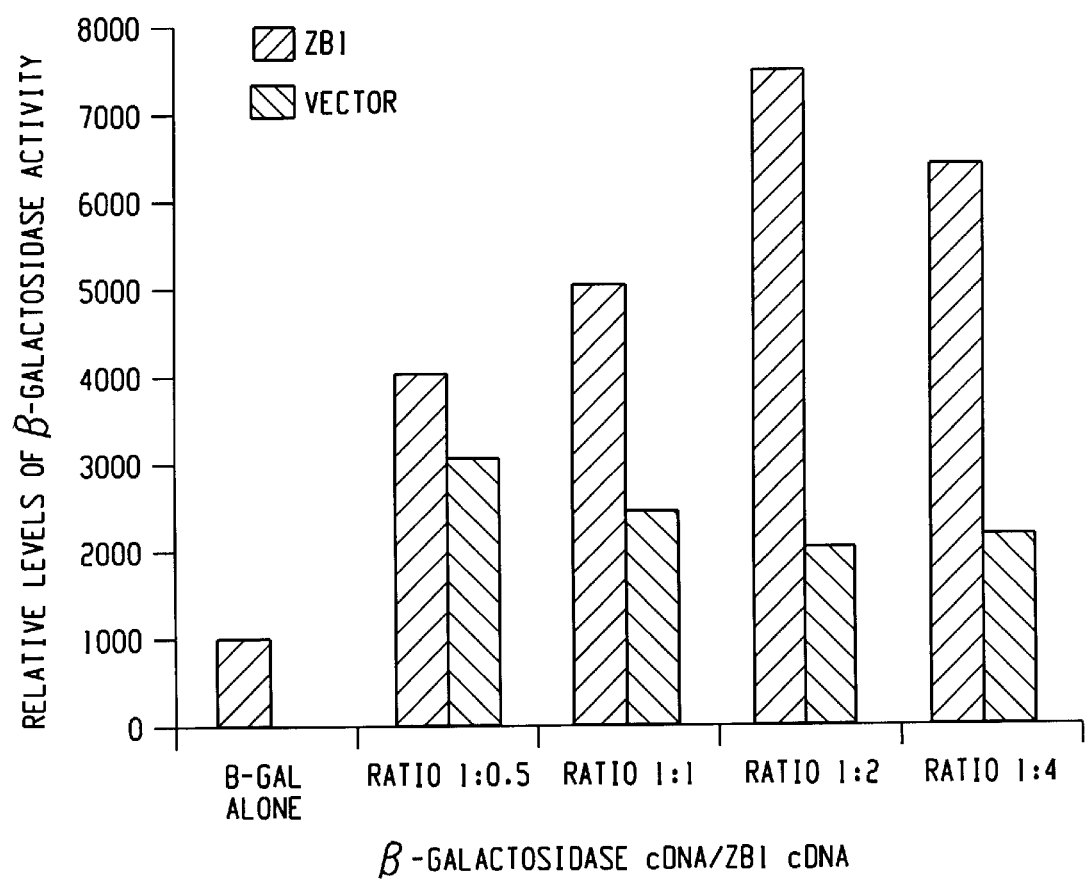
FIG. 9. A dominant negative mutant of murine RNase L, RNase L ZB1, enhances β-galactosidase expression in PKR$^{-/-}$ cells. PKR$^{-/-}$ cells were transiently co-transfected, as describe in Methods, with 2 μg of pSV-β-galactosidase and different amount of pCDNA/ZB1 or pCDNA. After 18 h, β-galactosidase activity was measured. Values are an average of an experiment performed in duplicate. Data reported as relative absorbance units per $10^6$ cells.

Galactosidase activity was measured as described in Example 1. As shown in FIG. 9, translation of exogenous proteins is enhanced in $PKR^{-/-}$ cells that have also been transfected with a dominant negative RNase L mutant, ZB1. The ZB1 construct enhanced by about 7-fold levels of β-galactosidase activity in the $PKR^{-/-}$ cells. The vector alone had a smaller, 2- to 3-fold stimulatory effect by an unknown mechanism.

EXAMPLE 7

Producing High Levels of Recombinant Exogenous Proteins in RNase $L^{-/-}$ cells by Co-transfection with a DNA Encoding Adenovirus VAI RNA.

Figure 7:
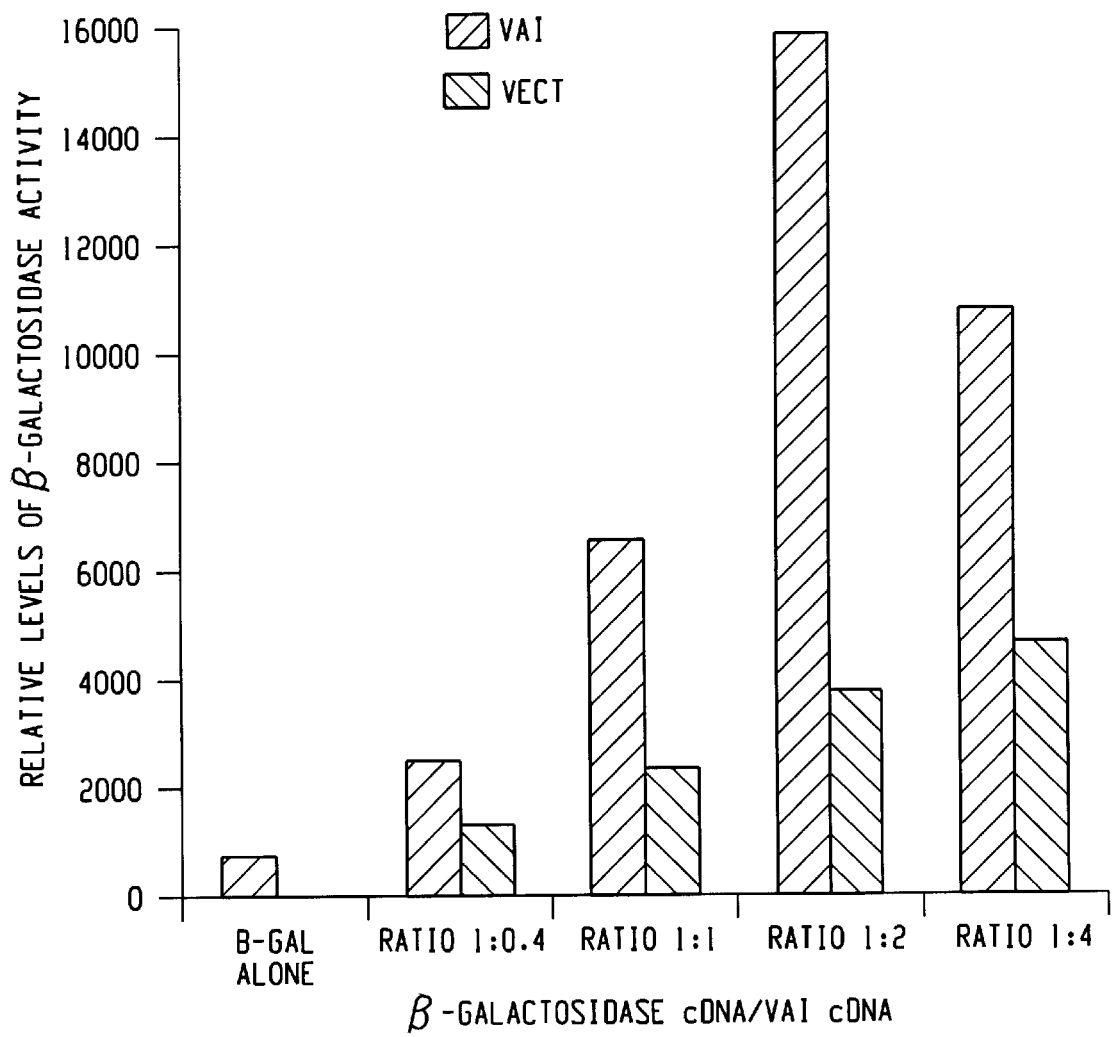
FIG. 7. Adenovirus VAI RNA greatly enhances β-galactosidase expression in RNase L$^{-/-}$ cells. RNase L$^{-/-}$ cells were transiently cotransfected with 2 μg of pSV-β-galactosidase and different amount of pAdVAntage (Promega Co.) encoding VAI RNA or pBR322 vector control. After 18 h, β-galactosidase activity was measured. β-galactosidase activity is per $10^6$ cells. Values are averages from an experiment performed in duplicate.

RNase $L^{-/-}$ MEF cells prepared as described above were co-transfected with β-galactosidase cDNA and different concentrations of pAdVAntage vector containing base pairs 9,831 to 11,555 of the adenovirus type 2 genome encoding the virus-associated RNA genes VAI and VAII (Promega). Galactosidase activity was measured as described in Example 1. As shown in FIG. 7, expression of β-galactosidase was enhanced up to about 20-fold by co-transfecting VAI cDNA in the RNase $L^{-/-}$ cells. (Also See FIG. 12)

EXAMPLE 8

Producing High Levels of Recombinant Exogenous Proteins in $PKR^{-/-}$ Cells by Co-transfection with a DNA Encoding Adenovirus VAI RNA.

$PKR^{-/-}$ MEF cells prepared as described above in Example 4 were co-transfected with pSV β-galactosidase vector (4 µg, unless otherwise indicated) and 4 µg of pAdVAntage vector containing base pairs 9,831 to 11,555 of the adenovirus type 2 genome encoding the virus-associated RNA genes VAI and VAII (Promega). Galactosidase activity was measured as described in Example 1.

Figure 8:
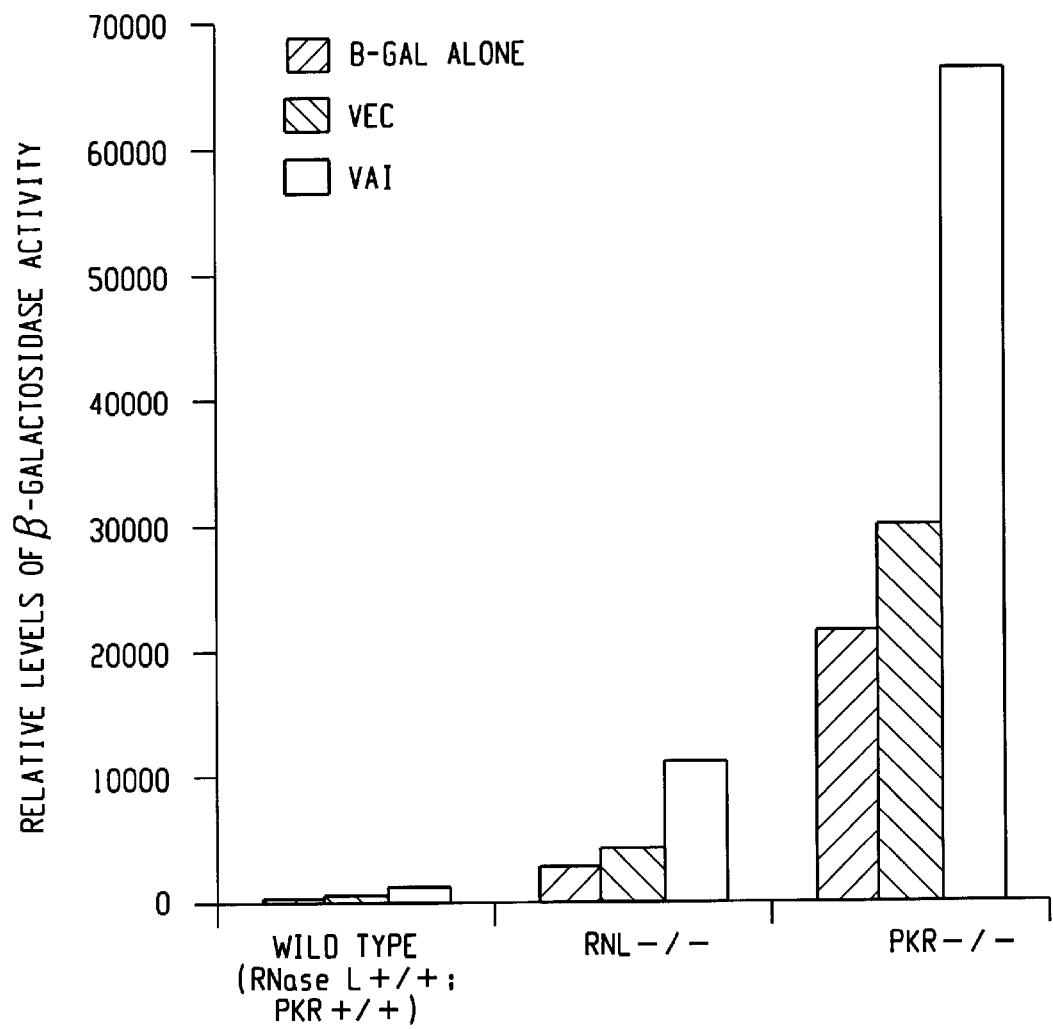
FIG. 8. VAI RNA enhances β-galactosidase expression in wild type, RNase L(RNL)$^{-/-}$ and in PKR$^{-/-}$ cells. Cell were transiently cotransfected with 4 μg of pSV-β-galactosidase and 4 μg of pAdVAntage or 4 μg of pBR322 separately. After 18 h, β-galactosidase activity was measured. Values are averages from 2 experiments performed in duplicate. Data are reported as relative absorbance units per $10^6$ cells.
Figure 12:
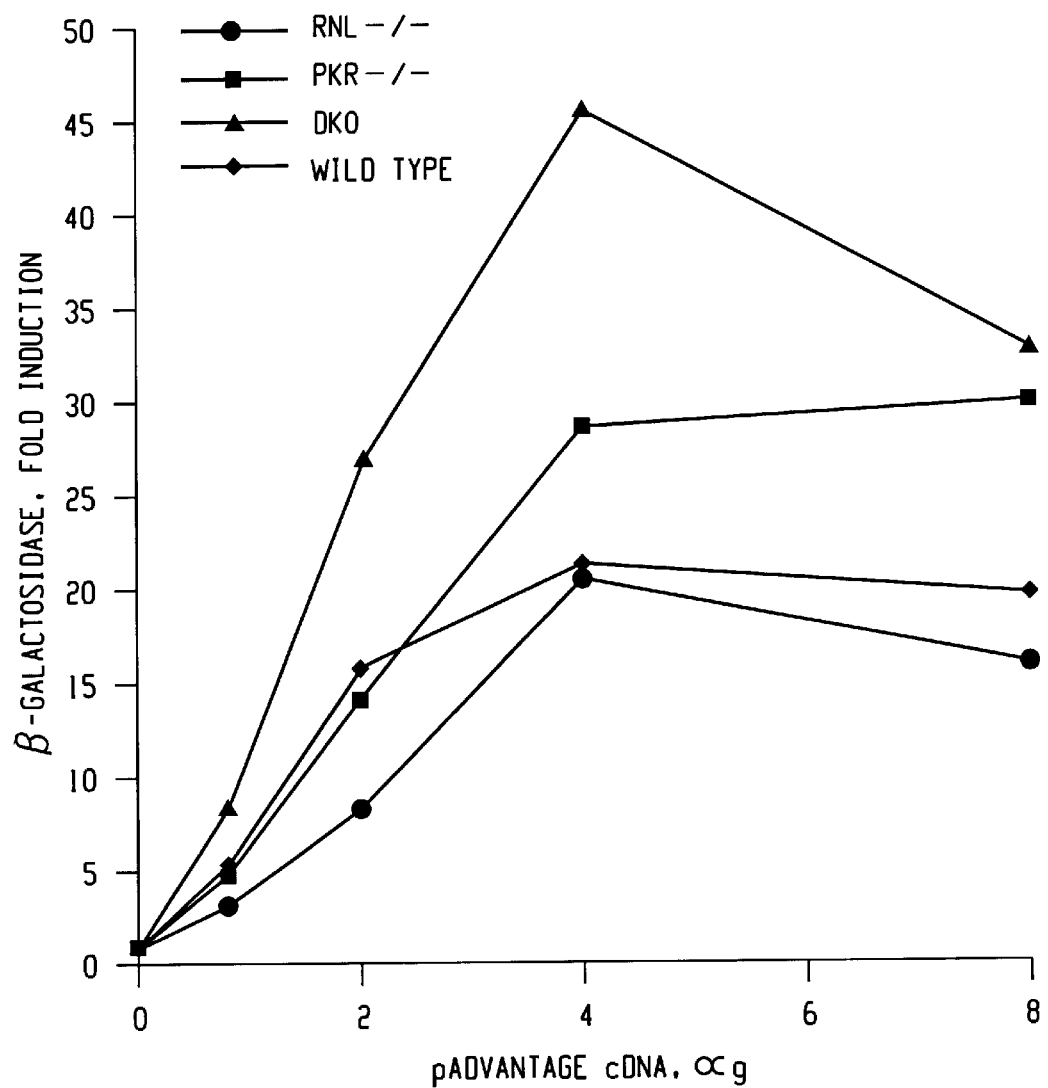
FIG. 12 is a graph showing that VAI RNA enhances β-galactosidase expression in wild type, RNase L(RNL)$^{-/-}$, PKR$^{-/-}$, and DKO cells. Cell were transiently cotransfected with 4 μg of pSV-β-galactosidase and 4 μg of pAdVAntage or 4 μg of pBR322 separately. After 18 h, β-galactosidase activity was measured.

Surprisingly, VAI RNA enhanced translation in the $PKR^{-/-}$ cells (FIGS. 8 and 12). These results suggest that the mechanism for the protein synthesis promoting activity of VAI RNA includes a mode of action other than PKR inhibition. In the $PKR^{-/-}$ cells co-expressing VAI RNA, the level of β-galactosidase activity was increased by 166-fold compared to the control cells and by 55-fold compared to the control $PKR^{+/+}$ cells co-expressing VAI RNA.

EXAMPLE 9

Producing High levels of Recombinant Exogenous Proteins DKO Cells by Co-transfection with a DNA Encoding Adenovirus VAI RNA.

DKO cells prepared as described above in Example 1 were co-transfected with pSV β-galactosidase vector (4 µg, unless otherwise indicated) and 4 μg of pAdVAntage vector containing base pairs 9,831 to 11,555 of the adenovirus type 2 genome encoding the virus-associated RNA genes VAI and VAII (Promega). Galactosidase activity was measured as described in Example 1.

Surprisingly, VAI RNA enhanced translation in the DKO cells (FIG. 12). In the DKO cells co-expressing VAI RNA, the level of β-galactosidase activity was increased by 45.8-fold compared to the control cells and by 2.2 fold compared to the control cells co-expressing VAI RNA.

COMPARATIVE EXAMPLE

The rates of endogenous protein synthesis in wild-type fibroblasts, PKR$^{-/-}$ cells, and RNase L$^{-/-}$ cells was measured by measuring the incorporation of radiolabeled methionine into the total protein of these cells during a one hour incubation period. Therates of endogenous protein synthesis in each of these cell types following transfection with a control vector or with a vector containing a sequence encoding the adenovirus VAI RNA was also determined. Specifically, 10×10$^5$ cells of each cell type were transfected with pAdVAntage vector or pBR322 (control vector) as described above. At 18 hours after transfection, the cells were incubated in medium containing 100 μCi/ml of $^{35}$S-L-methionine in serum free medium for 1 h at 37° C. Following removal of the media, the cell layers were rinsed four times with 2 ml cold 5%TCA to precipitate the proteins in the cells. The precipitated protein in each cell layer was then solubilized in 0.25 M NaOH at room temperature, neutralized, and the radioactivity determined in a liquid scintillation counter. The amount of radioactivity, obtained by averaging the results from three separate studies, incorporated into protein of the transfected and non-transfected cells is shown in Table 1 below.

TABLE 1

|  | wild type (10$^6$ cpm/ 10$^5$ cells) | PKR-/- (10$^6$ cpm/ 10$^5$ cells) | RNL-/- (10$^6$ cpm/ 10$^5$ cells) | DKO (10$^6$ cpm/ 10$^5$ cells) |
|---|---|---|---|---|
| lipofectamine plus alone | 4.1 | 2.8 | 3.9 | 2 |
| pADVAntage (VAI,II) vector | 2.6 | 2 | 1.9 | 1.2 |
| pBR322 (vector control) | 3.1 | 2.9 | 3 | 1.2 |

As shown in Table 1, endogenous protein synthesis was not enhanced in PKR$^{-/-}$ cells or RNase L$^{-/-}$ cells as compared to wild-type cells. Moreover, endogenous protein synthesis was not enhanced in any of these three cell types by transfecting these cells with a nucleic acid encoding adenovirus VA I RNA and adenovirus VA II RNA.

The radiolabeled protein produced during a one hour incubation of cells from each cell type was also assayed by 10% sodium dodecyl sulfate-polyacrylamide gel electrophoresis. The results, determined by visual observation, confirmed those shown in Table 1.

While the methods and mutant cells for producing high levels of recombinant protein have been described to some degree of particularity, various adaptations and modifications can be made without departing from the scope of the invention as defined in the appended claims.

What is claimed is:

1. An isolated mutant mouse cell for producing high levels of exogenous, recombinant protein, wherein said mutant mouse cell has a homozygous disruption in the RNase L gene thereof and in the PKR gene thereof, and wherein said mutant mouse cell lacks biologically active RNase L enzyme and biologically active PKR enzyme.

2. A method for producing high levels of an exogenous, recombinant protein in vitro, comprising:
 a) providing an isolated mutant mouse cell having a homozygous disruption in its RNase L gene, or in both its RNase L gene and its PKR gene, wherein said mutant mouse cell either lacks biologically active RNase L enzyme alone, or lacks both biologically active RNase L enzyme and biologically active PKR enzyme;
 b) introducing a first nucleic acid encoding the exogenous protein into the mutant mouse cell;
 c) expressing said exogenous protein in said cell; and
 d) isolating said exogenous protein from said cell.

3. The method of claim 2 wherein said mutant mouse cell has a homozygous disruption in its RNase L gene and in its PKR gene, and further, comprising:
 introducing a second nucleic acid encoding adenovirus VAI RNA or VA II RNA into said cell, and co-expressing said exogenous protein and said adenovirus RNA.

4. The method of claim 2, wherein said mutant mouse cell has a homozygous disruption in its RNase L gene, and further comprising:
 introducing a second nucleic acid encoding adenovirus VAI RNA or adenovirus VA II RNA into said cell, and co-expressing said exogenous protein and said adenovirus RNA.

5. The method of claim 2, wherein said mutant mouse cell has a homozygous disruption in its RNase L gene, and further comprising:
 introducing a second nucleic acid encoding a dominant negative PKR polypeptide into said cell, and co-expressing said exogenous protein and said dominant negative PKR polypeptide.

6. The method of claim 5, further comprising introducing a third nucleic acid encoding adenovirus VAI RNA or adenovirus VA II RNA into said cell, and co-expressing said exogenous protein, said dominant negative PKR polypeptide, and said adenovirus RNA.

7. A method for producing high levels of an exogenous, recombinant protein in vitro, comprising:
 a) providing an isolated mutant mouse cell having a homozygous disruption in its PKR gene, wherein said mutant mouse cell lacks biologically active PKR enzyme;
 b) introducing a first nucleic acid encoding the exogenous protein into the mutant mouse cell;
 c) expressing said exogenous protein in said cell; and
 d) isolating said exogenous protein from said cell.

8. A method for producing high levels of an exogenous, recombinant protein in vitro, comprising:
 a) providing an isolated mutant mouse cell having a homozygous disruption in its PKR gene, wherein said mutant mouse cell lacks biologically active PKR enzyme;
 b) introducing a first nucleic acid encoding the exogenous protein into the mutant mouse cell;
 c) introducing a second nucleic acid encoding adenovirus VAI RNA or adenovirus VA II RNA into said cell;
 d) co-expressing said exogenous protein and said adenovirus RNA; and
 e) isolating said exogenous protein from said cell.

9. A method for producing high levels of an exogenous, recombinant protein in vitro, comprising:
 a) providing an isolated mutant mouse cell having a homozygous disruption in its PKR gene, wherein said mutant mouse cell lacks biologically active PKR enzyme;
 b) introducing a first nucleic acid encoding the exogenous protein into the mutant mouse cell;
 c) introducing a second nucleic acid encoding a dominant negative RNase L polypeptide into said cell;
 d) co-expressing said exogenous protein and said dominant negative RNase L polypeptide; and
 e) isolating said exogenous protein from said cell.

10. The method of claim 9 further comprising:
 introducing a third nucleic acid encoding adenovirus VAI RNA or adenovirus VA II RNA into said cell, and co-expressing said exogenous protein, said dominant negative RNase L polypeptide, and said adenovirus RNA.

11. A method for preparing an isolated mutant mouse cells for producing high levels of recombinant proteins in vitro, comprising:
 a) intercrossing a first mouse with a second mouse, said first mouse having a heterozygous disruption in its RNase L gene and a heterozygous disruption in its PKR gene, said second mouse having a heterozygous disruption in its PKR gene and a heterozygous disruption in its RNase L gene;
 b) characterizing the embryos produced by step (a) to identify an embryo having an RNase $L^{-/-}$: $PKR^{-/-}$ genotype; and
 c) isolating somatic cells from the embryo having said RNase $L^{-/-}$: $PKR^{-/-}$ genotype.

12. The method of claim 11 wherein said somatic cells are fibroblasts.

* * * * *

UNITED STATES PATENT AND TRADEMARK OFFICE
CERTIFICATE OF CORRECTION

PATENT NO. : 6,762,038 B1
DATED : July 13, 2004
INVENTOR(S) : Robert H. Silverman et al.

It is certified that error appears in the above-identified patent and that said Letters Patent is hereby corrected as shown below:

<u>Title page,</u>
Item [75], Inventors, please delete "OH (US)" and insert -- Ontario (CA) --.

Item [57], ABSTRACT,
Line 2, please delete "endonbonuclease" and insert -- endoribonuclease --.
Line 16, please delete "hating" and insert -- having --.

Signed and Sealed this

Twenty-first Day of September, 2004

JON W. DUDAS
*Director of the United States Patent and Trademark Office*